(12) United States Patent
Pathak et al.

(10) Patent No.: US 8,273,327 B2
(45) Date of Patent: Sep. 25, 2012

(54) RADIO-OPAQUE COMPOUNDS, COMPOSITIONS CONTAINING SAME AND METHODS OF THEIR SYNTHESIS AND USE

(75) Inventors: Chandrashekhar P. Pathak, Phoenix, AZ (US); Sanjay M. Thigle, Kalyan (IN)

(73) Assignee: Pathak Holdings, LLC, Phoenix, AZ (US)

( * ) Notice: Subject to any disclaimer, the term of this patent is extended or adjusted under 35 U.S.C. 154(b) by 119 days.

(21) Appl. No.: 12/840,376

(22) Filed: Jul. 21, 2010

(65) Prior Publication Data

US 2010/0290995 A1 Nov. 18, 2010

Related U.S. Application Data

(63) Continuation of application No. 10/914,701, filed on Aug. 9, 2004, now Pat. No. 7,790,141.

(60) Provisional application No. 60/494,340, filed on Aug. 11, 2003.

(51) Int. Cl.
*A61K 51/00* (2006.01)
*A61M 36/14* (2006.01)

(52) U.S. Cl. .................................... 424/1.89

(58) Field of Classification Search .............. 424/1.11, 424/1.65, 1.81, 1.85, 1.89, 9.1, 1.25, 1.49, 424/1.69, 1.73, 9.2
See application file for complete search history.

(56) References Cited

U.S. PATENT DOCUMENTS

| | | | |
|---|---|---|---|
| 5,384,333 A | 1/1995 | Davis et al. | |
| 5,410,016 A | 4/1995 | Hubbell et al. | |
| 5,514,379 A | 5/1996 | Weissleder et al. | |
| 5,565,215 A | 10/1996 | Gref et al. | |
| 5,567,410 A | 10/1996 | Torchilin et al. | |
| 5,824,333 A | 10/1998 | Scopelianos et al. | |
| 6,174,330 B1 | 1/2001 | Stinson | |
| 6,475,477 B1 | 11/2002 | Kohn et al. | |
| 6,514,947 B2 * | 2/2003 | Rolland et al. | 514/44 R |
| 6,599,448 B1 * | 7/2003 | Ehrhard et al. | 252/582 |
| 7,790,141 B2 * | 9/2010 | Pathak et al. | 424/1.89 |

* cited by examiner

*Primary Examiner* — D L Jones
(74) *Attorney, Agent, or Firm* — Maschoff Gilmore & Israelsen

(57) ABSTRACT

Radio-opaque biodegradable compositions are formed by modifying terminal groups of synthetic and natural biodegradable polymers such as polylactones with iodinated moieties. The biodegradable property of the compositions renders them suitable for use in medical field such as drug delivery, imaging. Compounds disclosed in this invention exist as neat liquid. Certain compositions disclosed in this invention form hydrophobic iodine rich domains when dissolved in water, such domains provide better contrasting properties as well as ability to dissolve hydrophobic bioactive drugs. Certain iodinated moieties disclosed in the invention are capable of cross linking natural proteins in situ in presence of suitable catalysts and co-catalysts.

21 Claims, 14 Drawing Sheets

RADIO-OPAQUE COMPOUNDS, COMPOSITIONS CONTAINING SAME AND METHODS OF THEIR SYNTHESIS AND USE

RELATED APPLICATIONS

This application is a continuation of U.S. patent application Ser. No. 10/914,701, filed Aug. 9, 2004, now U.S. Pat. No. 7,790,141, which claims priority of U.S. Provisional Application No. 60/494,340 filed Aug. 11, 2003, each of which are hereby incorporated herein by reference.

BACKGROUND

This present invention relates to biodegradable radio-opaque compounds that can be used as contrast agents in medical imaging, surgical markers and for localized drug delivery. The invention also relates to radio-opaque compounds, compositions containing such compounds and methods of their synthesis and use.

Definitions:

All scientific and technical terms used herein have the same meaning as is commonly understood by one skilled in the synthetic polymer chemistry, polyethylene glycol modification chemistry, controlled drug delivery and synthetic biodegradable chemistry art, and to which this invention belongs; unless it is defined specifically for this invention.

"Oligomers" are defined as low molecular weight polymeric compounds. In this invention, oligomers may be defined as polymeric compounds with molecular weight between 40-2000 Daltons.

"Cross-linked material" is meant to denote the conversion of a soluble material to an insoluble state. The crosslinked material may still be in a highly hydrated state.

"In situ" is meant to denote at a local site, especially within or in contact with living organisms, tissue, organs, or the body.

"Bioactive" as used herein, refers to one or all of the activities of a compound that show pharmacological or biological activity in human or animal body. Such biological activity is preferred to have therapeutic effect. The bioactive compounds that can be used include, but not limited to: antiviral agents; antiinfectives such as antibiotics; antipruritics; antipsychotics; cholesterol or lipid reducing agents, cell cycle inhibitors, anticancer agents, antiparkinsonism drugs, HMG-CoA inhibitors, antirestenosis agents, antiinflammatory agents; antiasthmatic agents; antihelmintics; immunosuppressives; muscle relaxants; antidiuretic agents; vasodilators; nitric oxide, nitric oxide releasing compounds, beta-blockers; hormones; antidepressants; decongestants; calcium channel blockers; growth factors such as bone growth factors, wound healing agents, analgesics and analgesic combinations; local anesthetics agents, antihistamines; sedatives; angiogenesis promoting agents; angiogenesis inhibiting agents; tranquilizers and the like. Cellular elements which be used for therapeutic use such as mammalian cells including stem cells, cellular components or fragments, enzymes, DNA, RNA, genes may also be included as bioactive components.

"Biodegradable" is meant to denote a material that will degrade in a biological environment by either a biologically assisted mechanism, such as an enzyme catalyzed reaction or by a chemical mechanism which can occur in a biological medium, such as hydrolysis.

"Biostable" is meant to denote a high chemical stability of a compound in an aqueous environment, which is similar to the environment, found in the human body such as phosphate buffered saline (pH 7.2).

"Injectable composition" means any polymeric or non-polymeric composition that can be injected as a liquid and converted into solid inside a human body using minimally invasive surgical devices.

Polyethylene glycol (PEG) or polyethylene oxide (PEO) refers to the same polymer which is made by polymerization of ethylene oxide.

Polymeric nomenclature used in this patent application such as poly (lactic acid) or polylactic acid or polylacticacid refer to the same polymer, unless otherwise stated clearly. This is also true for all others polymers referred in this patent application.

The radio-opaque nature of many compounds allows them to be traced within a human or an animal body and therefore such compounds find application in medical diagnostics and pharmaceutical field. Some of the applications of such radio opaque compounds include medical imaging applications such as x-rays, angiography, urography, phlebography and drug delivery at a localized site.

In medical imaging techniques such as X-ray imaging, attenuation of soft tissue by x-ray radiation can be improved by exogenously administering a radio-opaque compound, which gets distributed in the tissue to be imaged. The infused compound preferentially absorbs x-ray radiation in the tissue and therefore improves quality of the image. Such improved image results in better diagnosis of the medical condition.

It is desired that such compounds should mix with the body fluids without causing significant change in the local chemical environment such as osmolarity, which is concentration of the solute per unit of total volume of solution and pH, should be economically feasible, chemically stable, highly water soluble, readily injectable with low viscosity and a ready to inject solution, biologically inert and should be removable safely and completely by the body.

The radio opaque compounds reported in the prior art generally fall into two categories: ionic and non-ionic. The ionic monomeric compounds used as contrast media for intravascular use have an osmolarity seven to eight times that of normal human blood. This hyper-osmolarity is partly believed to be responsible for several subjective and objective adverse effects such as pain, endothelial damage, thrombosis and thrombophlebitis, disturbance of the blood-brain barrier, bradycardia in cardioangiography and increased pressure in the pulmonary circulation. On the other hand, non-ionic compounds such as Iohexol, Iopamidol, metrizamide are formulated as less hyperosmolar solutions. However, the current non-ionic radio opaque compounds are much more expensive and exhibit relatively high rate of adverse events. In a recent small clinical study, two non-ionic media containing Iohexol and Ioversol were compared. More than 10% patients, receiving either Iohexol or Ioversol reported adverse events, which were categorized from mild to moderate to severe. These events included dizziness, pruritus, apnea, fever, purpura, blurred vision, headache, urticaria, congestion, lightheadedness, vertigo, cough, metallic taste, disorientation, and nausea. Hence, the side effects of these ionic as well as non-ionic contrast agents cannot be overruled.

U.S. Pat. No. 5,746,998 titled "Targeted co-polymers for radiographic imaging" describes polymeric compounds such as diblock copolymers capable of forming micelles for medical imaging. The block copolymers, a combination of two polymers, and high molecular weight are essential to form micelles. Such polymers require several multistep synthesis procedures. In addition, water soluble biologically intert polymers such as polyethylene oxide or poly (vinyl pyrrolidinone), with molecular weight above 20,000 g/mol are not eliminated by the body and therefore are stored inside the body. Thus high molecular weight polymers above 20,000 are considered as non-degradable permanent implants. On the other hand, polyethylene glycol with a molecular weight below 300 is insoluble in water. Water solubility is considered essential for safe removal of the compound. Many derivatives of polyethylene oxide such as polyethylene glycol succinate based derivatives, glutaric acid based derivatives and hydroxy acid based derivatives undergo substantial hydrolysis and degradation when stored in water for prolonged periods of time. Such degradation leads to unstable formulations and may have toxic effects on the human body.

Also, ionized polymers used for medical imaging applications can increase the osmolarity of the injectable solution with their counter ions. This may lead to several adverse effects as pain, endothelial damage, and the like. For example, polylysine is considered as a charged polymer and must be ionized to bring its pH to physiological range.

In addition, polyethylene glycol (PEG) based compounds used for these applications are also susceptible for oxidative reaction, which can form toxic peroxide radicals. These PEG based compounds must be combined with antioxidants to improve shelf life and prevent oxidative related reactions.

Along with medical imaging, some of the radio-opaque polymers that are biodegradable have received considerable interest in the medical and pharmaceutical field, as they can perform temporary therapeutic function and are eliminated from the body once the therapeutic function has been accomplished. Some of the well-known applications of biodegradable polymers include surgical sutures, staples or other wound closure devices, as a carrier for bioactive substances for controlled drug delivery etc. Among the biodegradable polymers reported in the prior art, polymers prepared from hydroxy acids and/or polylactones have received much attention due to their degradability and toxicological safety. Homopolymers and copolymers based on the l-lactic acid, dl-lactic acid and glycolic acid are among the most widely used polymers for medical applications. These polymers can be formulated into variety of physical forms such as fibers or filaments with acceptable mechanical properties, degradation profile and non-toxic degradation products.

To visualize the deployment of bioabsorbable implantable devices in the human or animal body, many surgical procedures are performed with the aid of fluoroscopic angiography. However, most biodegradable polymers used in current clinical practice have poor visibility when viewed using standard medical imaging equipment. The absorbable polymeric material may be visualized if they are radio-opaque and offer radiographic contrast relative to the body. To make the absorbable polymer radio-opaque, it must be made from a material possessing radiographic density higher than surrounding host tissue, and have sufficient thickness to affect the transmission of radiations and produce a contrast in the image. To improve the visualization, the biodegradable polymer must be chemically and physically modified.

U.S. Pat. No. 6,174,330 titled "Bioabsorbable marker having radio-opaque constituents" discloses use of bioabsorbable polymer mixed with non-absorbable radio-opaque moieties such as heavy metal compounds mixed with the absorbable polymer. U.S. Pat. No. 6,475,477 titled "Radio-opaque polymer biomaterials" discloses tyrosine derived radio-opaque polymers.

However, current technologies may not be able provide radio-opaque biodegradable polymers that are degraded and completely eliminated by the body and also have good visibility when administered in a human or an animal body.

The above-mentioned limitation linked to biodegradable radio-opaque polymers is also applicable to Minimal Invasive Surgery (MIS) techniques. Minimally invasive surgery (MIS) encompasses laparoscopy, thoracoscopy, arthroscopy, intraluminal endoscopy, endovascular techniques; catheter based cardiac techniques such as balloon angioplasty, interventional radiology and the like. These procedures allow mechanical access to the interior of the body with the least possible perturbation of the patient's body. Many MIS procedures involve very small mechanical tools such as catheters or trocars that are manipulated outside the patient's body but are capable of performing their function within the patient's body. Biodegradable polymers that can be used with MIS procedures are becoming increasingly important. These polymers are used as sutures, surgical clips, staples, sealants, tissue coatings, implants and drug delivery systems. The polymers that are used with MIS applications are either preformed or are generated in-situ. However, the visibility of these polymers when administered in a human or an animal body is low. In many MIS applications, it is essential to transport the material at the surgical site. The radio-opacity helps to monitor the movement of implant from the site of implantation or degradation of implant. Radio-opacity also helps to locate and retrieved the biodegradable implant if necessary. Thus radio-opacity offers many useful functionalities, which may help to offer better medical treatments.

A need exists for radio-opaque polymers that are easily degraded in the body and have no side effects. There is also a need of polymers that have a good visibility under medical imaging scanners. There is further a need for injectable biodegradable polymeric compositions that are radio-opaque and can be used to deliver bioactive drugs using MIS techniques.

SUMMARY

In the light above discussion, it is the object of the present invention to provide oligomeric, homopolymeric, water soluble, hydrolytically stable and non-ionic compounds and compositions useful in medical diagnostic and pharmaceutical field.

Another object of this invention is to provide contrast agent compositions, which self assemble in water forming iodine rich domains for use in x-ray imaging and localized delivery of bioactive compounds.

Another object of this invention is to provide radio opaque compounds that are water soluble and exist as a neat liquid at temperature between 10° C. to 45° C.

Another object of this invention is to provide contrast media compositions that are stored and dispensed in biocompatible substantially non-aqueous medium.

Yet another objective of this invention is to provide synthesis methods for preparation of radio opaque compounds.

Yet another objective of this invention is to provide methods for preparation of compositions containing radio opaque compounds.

Another object of this invention is to provide polyether based compounds with iodinated xanthene moieties.

Another object of this invention is to provide polyether based radio-opaque biostable compositions for controlled drug delivery.

Another object of this invention is to provide methods and compositions tissue specific contrast enhancing compositions. More specifically, human antibodies, monoclonal human antibody whose functional groups are chemically reacted with iodinated compounds like triiodobenzene or xanthene derivatives. Another object of this invention is to provide methods and compositions of iodinated compounds with activated functional groups. Such activated compounds react with proteins under mild reaction conditions such as physiological conditions (PBS pH 7.2).

Another object of this invention to provide methods and compositions for radio-opaque natural polymers such as albumin, collagen, gelatin, antibodies, hyaluronic acid, chitosan and their use in medical application such as controlled drug delivery applications.

Another object of this invention to provide methods and compositions for radio-opaque proteins such as albumin, collagen, gelatin, antibodies wherein the modified proteins are soluble in water.

Another object of this invention to provide methods and compositions for radio-opaque proteins such as albumin, collagen, gelatin, antibodies wherein the modified proteins are crosslinked using zero length crosslinking agent.

Another object the invention is to provide methods and compositions of biodegradable polymers or biostable polymers, which are blended with iodinated compounds, more specifically with non-ionic or polymeric iodinated compounds.

Another object of this invention is to provide a radio-opaque composition that is thermosensitive in nature.

Another object of this invention is to provide radio-opaque biodegradable composition that can be formed in situ inside a human or animal body.

Another objective of the invention is to provide a kit for used as injectable crosslinkable radio-opaque formulation, wherein the constituents may be premixed just prior to surgical procedure and injected using MIS surgical technique.

Another object of this invention is to provide radio-opaque composition that can be gelled or solidified by physical crosslinking by change in phase.

Another object of this invention is to provide a process for treating a condition requiring the use of biodegradable medical device or pharmaceutical treatment, which comprises an injection into a body or body cavity, and a hydrophobic, biodegradable radio-opaque polymer.

Another object of this invention is to provide a method for treating a medical condition requiring the use of biodegradable medical device or pharmaceutical treatment, which comprises; an injection into a body or body cavity, and a hydrophobic, biodegradable polymer that is dissolved in a biocompatible solvent along with x-ray contrast agent.

Another objective of this invention is to provide an implantable or injectable composition comprising at least one biologically active compound in a hydrophobic radio-opaque biodegradable polymer.

Another object of this invention is to provide a completely biodegradable surgical biopsy marker.

Another object of this invention is to provide a surgical biodegradable biopsy marker that is visible in two or more medical imaging techniques.

Another object of this invention is to provide a biopsy marker wherein the biopsy marker has an outer skin made from hydrophobic biodegradable polymer and a hollow interior wherein the hollow interior is filled with one or more medical imaging agent.

Another object of this invention is to provide radio-opaque protein cross-linker.

Another objective of this invention is to provide a biodegradable or biostable radio-opaque coating composition for a biodegradable/biostable medical device such as a biodegradable/biostable stent, biodegradable/biostable suture, biodegradable/biostable spinal implants and cages, surgical markers biodegradable/biostable staple, clip.

BRIEF DESCRIPTION OF THE DRAWINGS

The preferred embodiments of the invention will hereinafter be described in conjunction with the appended drawings provided to illustrate and not to limit the invention, wherein like designations denote like elements, and in which.

DESCRIPTION OF PREFERRED EMBODIMENTS

Radio-Opaque Biodegradable Compounds and Compositions

Described herein are radio-opaque biodegradable polymeric compounds, which are used for medical applications. For these applications the polymers may be combined with a variety of materials. Examples of such materials include, but are not limited to, bioactive compounds, carrier mediums, medical devices, and the like. The radio-opaque polymeric compounds may be detected by medical imaging scanners such as X-ray scanners, Magnetic resonance Imaging (MRI) scanners, Nuclear magnetic Resonance (NMR) scanners and Ultrasound scanners. This invention also provides compositions and methods that provide radio-opaque protein cross-linkers.

Figure 1:
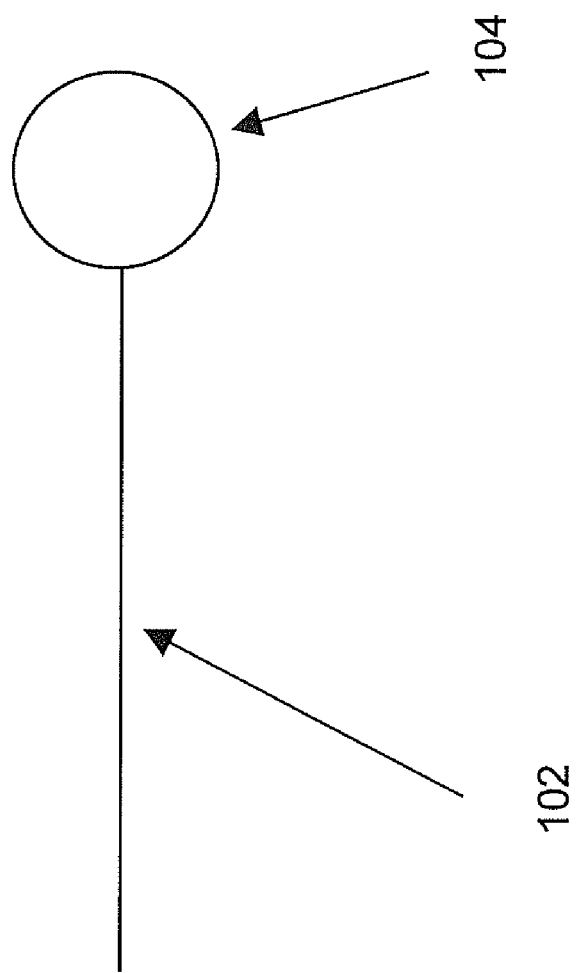
FIG. 1 shows schematically the constituents of the radio-opaque biodegradable polymeric compound.

FIG. 1 shows the constituents of the radio-opaque biodegradable polymeric compound. The radio-opaque polymeric compound comprises a biodegradable polymer 102 and a radio-radio-opaque iodinated moiety 104. Biodegradable polymer 102 is linked to iodinated moiety 104 using a biodegradable chemical bond. In various embodiments of the invention, iodinated moiety 104 is linked to an end of biodegradable polymer 102.

Figure 2:
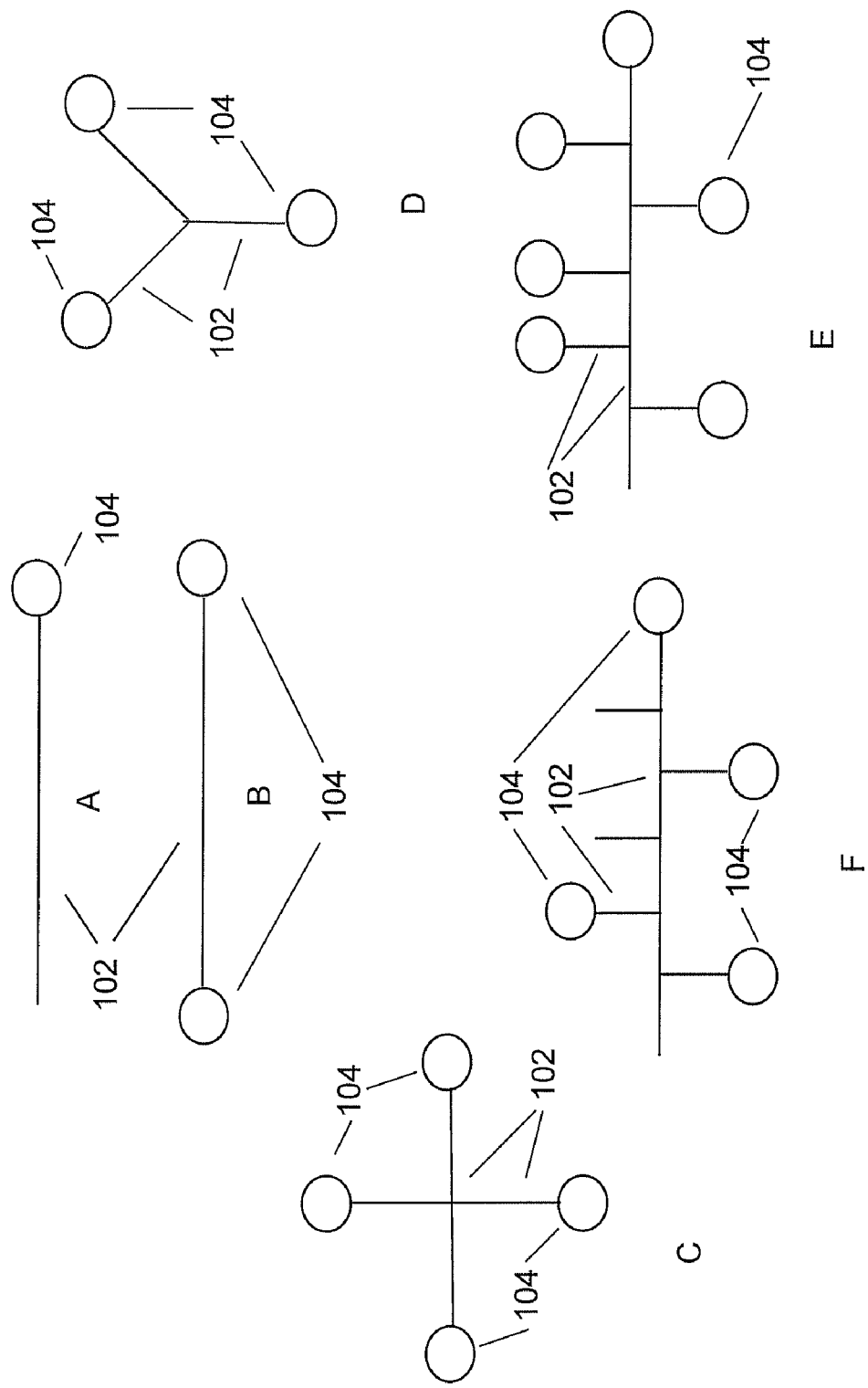
FIG. 2 shows schematically exemplary structures that constitute the biodegradable radio-opaque polymeric compound.

FIG. 2 shows exemplary structures of the biodegradable radio-opaque polymeric compound. The structures described in FIG. 2 have two parts, biodegradable region 102 and radio-radio-opaque iodinated moiety 104. Structures A and B represent a linear polymer with one or both ends of biodegradable region 102 modified with radio-radio-opaque iodinated moiety 104. Structure C shows, a branched or star shaped biodegradable polymer terminated with radio-radio-opaque iodinated moiety 104. In addition, structure D shows a multi-branched star shaped biodegradable polymer whose ends groups are substituted with radio-radio-opaque iodinated moiety 104. Structure E shows a graft type biodegradable polymer substituted with radio-opaque region 104. A graft like polymer can be synthesized by various methods known in the art. Examples of graft like polymers include copolymers of lactide and lysine, synthesized by methods known in the polymer chemistry art. The iodinated moiety and the graft shape biodegradable polymer may be linked using an amine functional side group. Structure F shows a multifunctional biodegradable polymer whose ends groups are partially substituted with radio-opaque iodinated moiety 104. In various embodiments of the biodegradable radio-opaque polymeric compound, the unsubstituted sites (as shown in Structure F) are attached to a drug or bioactive compound. This partial substitution is desirable to obtain suitable polymer properties.

In various embodiments, biodegradable region 102 includes polymers, copolymers or oligomers of: glycolide, dl-lactide, d-lactide, l-lactide, caprolactone, dioxanone and trimethylene carbonate; polyhydroxyacids, polylactic acid, polyglycolic acid, polyorthocarbonates, polyanhydrides, polylactones, polyaminoacids, and polyphosphates. The size or length of biodegradable region 102 is varied depending upon the applications desired. In addition, radio-opaque iodinated moiety 104 is selected from iodine-substituted compounds including triiodobenzoic acid, triiodophenol, erythrosine, rose bengal, and their derivatives. Examples of these derivatives include, 2,3,5-triiodobenzoic acid and 3,4,5-triiodophenol. More particularly, 3,5-Bis(acetylamino)-2,4,6-triiodobenzoic acid, 3,5-Diacetamido-2,4,6-triiodobenzoic acid may be used, and preferably 3,5-Diacetamido-2,4,6-triiodobenzoic acid may be used.

Preparation

The biodegradable radio-opaque polymeric compound of the invention is made using synthetic biodegradable polymer synthesis methods.

Table 1 illustrates exemplary reactants and their concentration used for making various biodegradable radio-opaque compositions.

TABLE 1

| Polymer Code | Biodegradable Polymer (BP) | Average Mol. wt. of BP (Daltons) | Iodinated Moiety (IM) | No. of end-groups modified | No. of iodine atoms per molecule | Iodine (%) |
| --- | --- | --- | --- | --- | --- | --- |
| BP101 | Polylactide | 4030 | Erythrosin | 3 | 12 | 37 |
| BP102 | Polycaprolactone | 4271 | Triiodobenzene | 5 | 15 | 44 |
| BP103 | Polycaprolactone | 1963 | Triiodobenzene | 2 | 3 | 39 |
| BP104 | Polylactide | 3366 | Triiodobenzene | 1 | 3 | 11.3 |
| BP104 | Polylactide | 9126 | Triiodobenzene | 1 | 3 | 4.17 |

The biodegradable polymers that may be used in the synthesis include polylactide, polycaprolactone, and polyglycolides. In addition, the iodinated moieties that are chosen for synthesis include derivatives of erythrosine and triiodobenzene. The radio-opaque moieties (as described in Table 1) may be solid, liquid, semi-solid, gel or wax type. The number of iodinated end groups and the concentration of iodine in the end compound may be varied based on the number of the iodinated end groups linked to the terminals of the biodegradable polymers. For example, Polycaprolactone (BP102) has 5 end groups modified with Triiodobenzene to achieve an iodine concentration of 44% by weight. In addition, the biodegradation of the compound will depend upon the type of biodegradable polymer used. For example, polycaprolactone generally degrade in 2-5 years, polylactide generally degrade in 6-24 months and polyglycolide generally degrade in six months. The copolymers of these and other lactones may have degradation time from one month to 5 years.

The iodinated end-capped polymers produced in accordance with the invention can attain desirable physical and chemical properties. These can be obtained by choosing structural features such as the nature of the end group, (hydrophobic or hydrophilic), the chain length and chemical structure of the end-group. The biodegradable polymeric segment can also have structural variables such as molecular weight and/or molecular weight distribution, the chemical nature, the repeating unit of polymer or copolymer, and the nature of end group.

Figure 3:
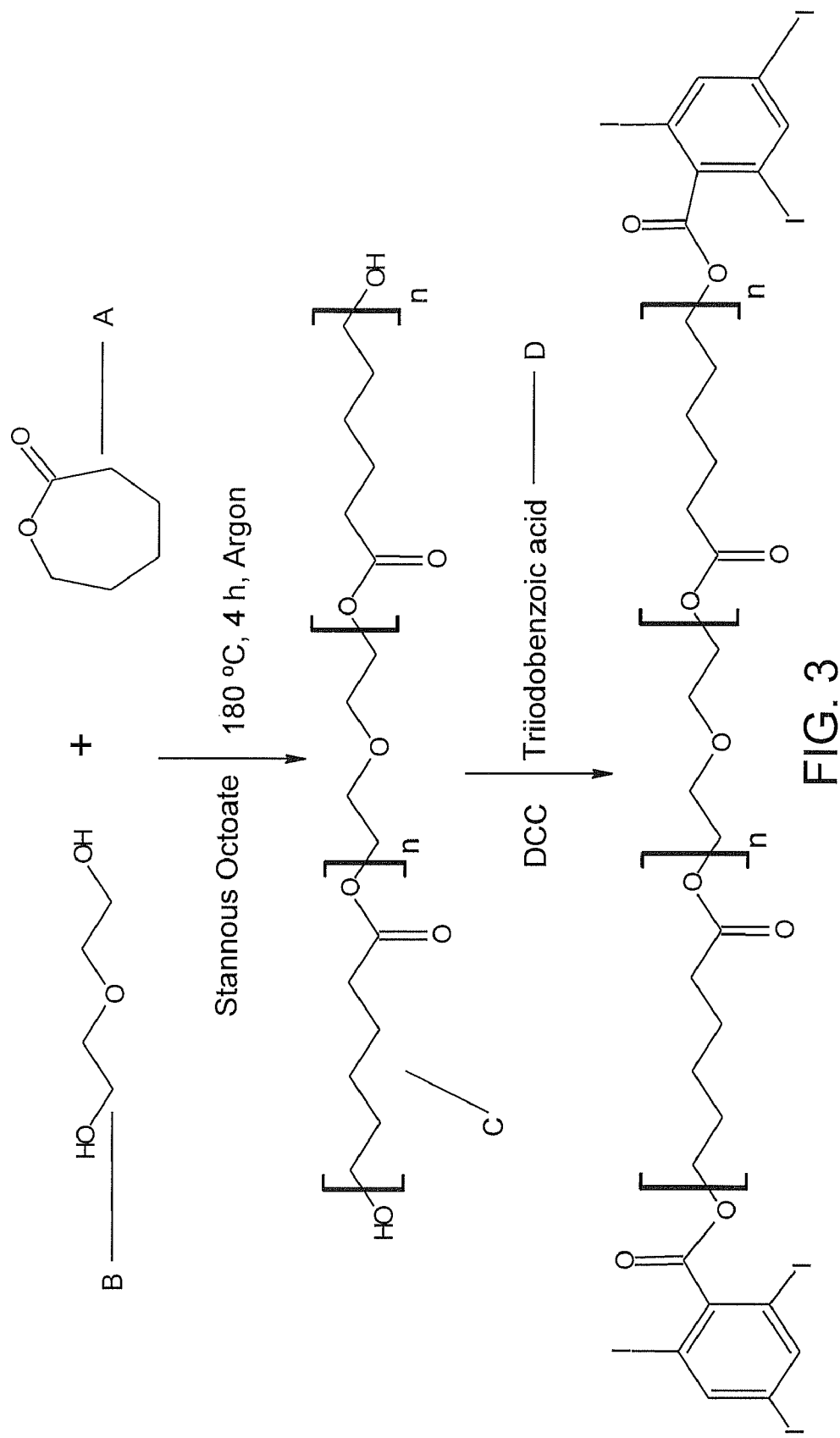
FIG. 3 describes an exemplary reaction procedure for synthesizing polycaprolactone terminated with triiodobenzoic acid ester.

FIG. 3 describes an exemplary reaction procedure for synthesizing polycaprolactone terminated with triiodobenzoic acid ester. The reaction begins with polymerization of caprolactone (A). The reaction is initiated by diethylene glycol (B) in the presence of stannous octoate at a temperature of 180° C. The reaction produces polycaprolactone diol (C), which has a molecular weight of 2000 Daltons and terminated with two hydroxyl groups. The polycaprolactone diol (C) produced is then esterified with Triiodobenzoic acid (D) in the presence of DCC as a catalyst. The resultant polymer is polycaprolactone terminated with two triiodobenzoic acid esters. Other variations of this synthesis are possible, such as copolymerization with glycolide or caprolactone to obtain a copolymer. This copolymer is then used in the subsequent reaction where terminal hydroxyl groups are esterified with triiodobenzoyl chloride. In another embodiment, a 5-arm polycaprolactone polymer is synthesized by ring opening polymerization of caprolactone. The reaction is initiated by xylitol. The 5 hydroxy groups on xylitol initiate polymerization, producing a star polymer with hydroxy end groups. The hydroxy end-groups are subsequently reacted with triiodobenzoic acid to produce ester of triiodobenzoic acid.

Figure 4:
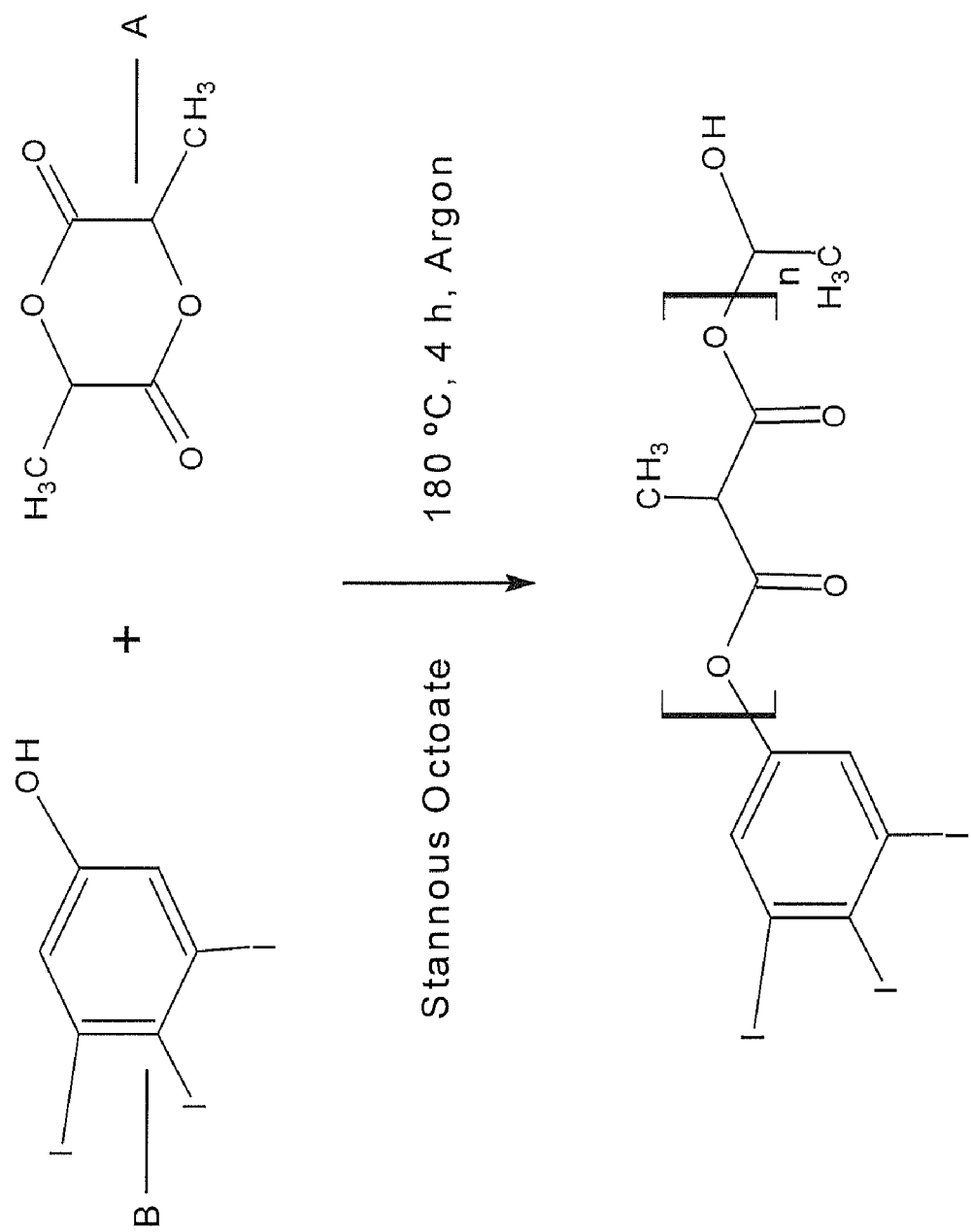
FIG. 4 describes an exemplary reaction procedure for polymerizing dl-lactide with triidophenol.

FIG. 4 describes an exemplary reaction procedure for polymerizing dl-lactide with triiodophenol or triiodobenzyl alcohol. In the reaction, the dl-lactide (A) ring is opened and polymerization is initiated by triiodophenol (B). The reaction is initiated in the presence of stannous octoate at a temperature of 180° C. In order to obtain a desired molecular weight of lactide or to control the degree of polymerization, a specific ratio of lactide to triiodophenol is chosen.

In another embodiment, trimethylol propane-triol is used to initiate the polymerization of lactide and caprolactone. The low molecular liquid polymer thus obtained was used in subsequent esterification reaction with Erythrosine. In another embodiment of the invention, graft type polymers are made by modifying lysine residues of gelatin or collagen chains.

In another embodiment, polyhydroxy iodinated compounds such as metrizamide, iopamidol, iopentol, iopromide, and ioversol are used to initiate the polymerization of lactones such as lactide and glycolide. The resultant polymer has triiodo group at the center, which provides radio-opaque properties. In another embodiment, triiodobenzyl alcohol or triiodophenol is used to initiate polymerization of cyclic lactone. Briefly, hydroxy group on the triiodobenzyl alcohol or triiodophenol is used to initiate polymerization of cyclic lactone monomers such as glycolide and caprolactone. The method does not require additional reactions to link iodinated moieties to the polymer. Some biodegradable polymers such as polylactic acid may also be synthesized by polycondensation of lactic acid. The terminal groups of such polymers may be modified with iodine containing compounds.

Radio-Opaque Protein Modifying Agents

This invention also describes a radio-opaque protein modifying agents and radio-opaque protein cross-linkers. These cross-linkers upon modification and/or cross-linking show improved visibility of the modified/cross-linked composition when viewed using medical imaging equipments.

Radio-opaque protein modifying agents and cross-linkers described in this invention have three parts including: at least one functional group (F) capable of reacting with protein preferably under mild conditions, and at least one radio-opaque chromophore (M) capable of strongly scattering/absorbing x-ray radiation. The two parts are linked through a third part (X).

The parts of the radio-opaque protein modifying agents and cross-linkers are represented by the following structural formula:

Where;

$n \geq 1$

F is a functional group reactive with collagen or protein under mild reaction conditions and preferably capable of reacting with free primary amine groups in the protein;

M is a chromophore that can absorb radiations. The preferred chromophores that are used for absorbing X-rays include, but not limited to: phenyl ring compounds such as 2,3,5-triiodobenzoic acid, 3,4,5-triiodophenol, erythrosine, rose bengal, 3,5-Bis(acetylamino)-2,4,6-triiodobenzoic acid, 3,5-Diacetamido-2,4,6-triiodobenzoic acid, heavy metal ion complexes, and the like.

X is an organic molecule/radical covalently linking F and X. X comprises Carbon-Carbon, Carbon-Hydrogen, Carbon-Nitrogen, Carbon-Oxygen, Carbon-Sulfur, Nitrogen-Hydrogen and Oxygen-Hydrogen covalent bonds. X may be polymeric or non-polymeric in nature.

In embodiments that do not require cross-linking, only one functional group (F) per molecule is chosen. This is done to avoid cross-linking of proteins. On the other hand, if cross-linking is desired, 2 or more functional groups are used.

The mild reactions conditions, under which the functional group (F) can react with proteins and form a chemical bond, include physiological conditions (PBS buffer, pH 7.2).

Functional groups that are reactive with collagen molecule and suitable for use may include, but not limited to, are: anhydride, isocyanate, n-hydroxysuccinimide, n-hydroxysulfosuccinimide, epoxy, aldehyde, and other collagen reactive functionalities known in the art.

Radio-opaque cross-linker/modifying agents according to the inventions include, but not limited to: activated monofunctional triiodobenzene derivatives such as n-hydroxysuccinimide esters, n-hydroxysulfosuccinimide esters of triiodobenzoic acid, 3,5-Diacetamido-2,4,6-triiodobenzoic acid or Diatrizoic acid and erythrosine.

Preparation

In an exemplary embodiment, the hydroxyl groups of commercially available X-ray contrast agent are converted into carboxylic acid group by reacting with succinic anhydride. The acid groups are then activated with n-hydroxysuccinimide ester or n-hydroxysulfosuccinimide to from a cross-linker. The n-hydroxysulfosuccinimide ester is preferred in many situations because it provides improved water solubility presumably due to sulfonate group on the n-hydroxysuccinimide ring. The activated acid groups then reacts with protein in aqueous medium under mild conditions.

In another embodiment, iohexol derivative are used to generate protein modifying agent/cross-linkers. Many hydroxy activated chemistries known in the polyethylene glycol modification chemistry are used to modify the Iohexol hydroxy groups; these include but not limited to: sulfonyl chloride activation chemistry, carbodiimide activation chemistry and the like. The three iodine atoms in activated iohexol derivative serve as X-ray absorbing chromophore. In addition, many iodinated compounds having multiple hydroxy groups can be used. These include but not limited to: metrizamide, iopamidol, iopentol, iopromide, iodixanol and ioversol.

After chemically bonding of Iohexol to the protein, the modified protein shows better X-ray contrasting ability when compared with unmodified protein. The X-ray contrasting ability will depend on the amount of organically bound iodine incorporated in the modified protein. The preferred amount of iodine incorporated in the protein range from 30 mg/g of protein to 400 mg/g of protein. The most preferred amount of iodine that is incorporated is in the range of 50 to 200 mg/g of protein.

Figure 6:
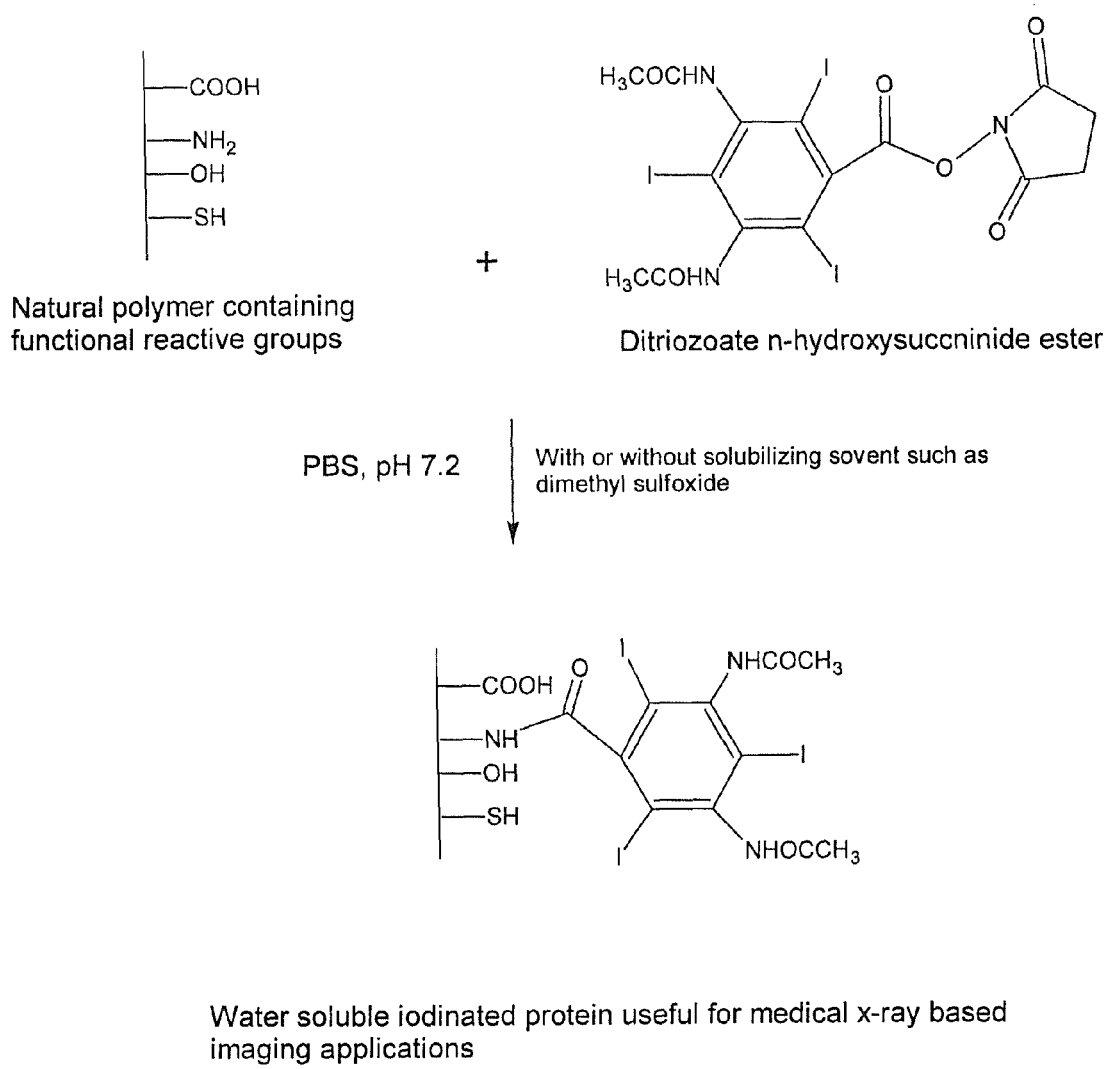
FIG. 6 illustrates an exemplary modification scheme for modification of natural polymer such as albumin or antibody using iodinated compound to produce a substantially non-crosslinked water soluble modified polymer.

In some medical applications such as tissue specific diagnostic imaging application, a radio-opaque protein that is water soluble is highly desirable. This invention provides methods and protein based water soluble radio-opaque compositions. In one exemplary embodiment, modification of albumin is done by n-hydroxysuccinimide ester benzoic acid or diatrizoic acid. The monofunctional modification reaction provides iodine group incorporation without chemical cross-linking (FIG. 6). The two amide group in diatrizoic acid help to enhance water solubility of modified protein. Therefore, modification of protein with diatrizoic acid is even more preferred. It is preferred to incorporate at least 5 to 40 percent organically bound iodine in the modified protein. 10 to 20 percent organically bound iodine incorporation is even more preferred. The water soluble iodinated proteins especially antibodies could be used in diagnostics applications. The water soluble radio-opaque protein can also be used for drug delivery and contrast medium applications.

In another approach, a radio-opaque polymerizable monomer or macromonomer may be used in polymerization and cross-linking of protein. For example, a polymerizable radio-opaque monomer may be obtained by esterification of tri-iodobenzoic acid and 2-hydroxyethyl methacrylate. The radio-opaque ester may be copolymerized and cross-linked with unsaturated group modified protein.

In one embodiment, the cross-linked radio-opaque protein is lyophilized. The lyophilization creates porosity in the protein hydrogel. The air entrapped in the porous structure is useful in creating a better image when viewed using ultrasonic imaging technique. The air in the porous hydrogel may be replaced by other biocompatible gas. The term "biocompatible gas" refers to any compound which is a gas or capable of forming a gas at physiological conditions present in the human or animal body (for example at 37° C., pH 7.2). The gas or their mixtures in any all proportions may be selected from the group comprising: oxygen, carbon dioxide, argon, nitrogen or fluorinated hydrocarbons. Among the fluorinated hydrocarbons, perfluoropropane or perfluorbutane are preferred. Octafluoropropane and dodecafluorobutane are most preferred. The use of carbon dioxide, oxygen and octafluoropropane or their mixtures are most preferred. The porosity along with its entrapped gas provides better contrast when viewed using ultrasonic medical imaging equipment, and the iodine incorporation provides visibility in X-ray imaging equipment. Therefore this material is visible in two different imaging techniques. Many hydrated materials usually have good visibility in magnetic resonance imaging technique. Thus a radio-opaque hydrogel with porosity with its entrapped air or gas might be useful in all three major medical imaging technologies. Such materials may have wide applications in MIS surgery. The gas may be filled inside the porous polymer by packaging under gaseous atmosphere. For example, the porous radio-opaque composition may be packaged under octafluoropropane or carbon dioxide and the package may be opened just prior to implantation.

In an embodiment of the invention, a cross-linkable hydrophobic biodegradable polymer such as made by free radical polymerization of acrylate end-capped polyhydroxy acid polymer and is used as a matrix for drug delivery. This polymer is made radio-opaque by adding a radio-opaque compound such as Metrizamide, iopamidol, iopentol, iopromide, and Ioversol prior to free radical cross-linking. The radio-opaque compound added is physically entrapped in the polyhydroxy polymer and makes the cross-linked polymer radio-opaque.

The radio-opaque crosslinked hydrogel compositions may potentially be used to obtain synthetic radio-opaque hydrogels. A thiol or mercapto group reaction with organic compounds containing unsaturated groups could also be used to obtain radio-opaque hydrogels. For example, a radio-opaque crosslinker/monomer containing two or more unsaturated groups can be reacted with synthetic polymer such as polyethylene glycol derivative containing two or more amine or thiol functional groups to obtain a crosslinked hydrogel. In another variation of this approach, unsaturated polyethylene glycol based monomers such as polyethylene glycol diacrylate or methacrylate may be reacted with iodinated compounds two or more thiol groups to obtain radio-opaque hydrogels.

Natural Polymer Based Compositions

The present invention also provides natural polymer based compositions and methods useful for making radio-opaque biodegradable implants. The compositions described in this invention may be formed in-situ during a surgical procedure or may be formed outside in a manufacturing or laboratory environment.

In one embodiment of the invention, a radio-opaque iodinated compound and a catalyst that promotes a chemical bond between a natural polymer and iodinated compound is injected in-situ to form a cross-linked natural polymer based radio-opaque hydrogel. The radio-opacity is due to iodine compound that is chemically bonded to the cross-linked natural polymer network.

In various embodiments of the invention, reaction between a natural polymer and an iodinated compound results in a biodegradable natural polymer based hydrogel. Examples of natural polymer include, but not limited to: natural peptides or polypeptides, albumin, collagen, gelatin, elastin, keratin, hyaluronic acid, sodium hyaluronate, chitosan, dextran, or their derivatives and analogs and the like. The preferred natural polymers are albumin, collagen, gelatin, hyaluronic acid or chitosan. The natural polymer may also be obtained from recombinant technology or source generally known in the biotechnology art. For example, recombinant albumin, collagen, gelatin hyaluronic acid may be obtained form commercial sources. Hyaluronic acid made by recombinant technology can be purchased from Genzyme Inc., Cambridge, Mass., USA. A preferred natural polymer is albumin obtained from natural or recombinant source at a concentration at 10-50% (w/w), more preferably between 20 to 45% (w/w) of the uncross-linked composition.

The preferred iodinated compound is water-soluble, is biocompatible, is aromatic with 3 or more iodine atoms per molecule and has functional groups capable reacting with natural polymers. Examples of preferred iodine compounds include, but not limited to: iohexol, metrizamide, iopamidol, 3,5-bis(acetylamino)-2,4,6-triiodobenzoic acid, iopentol, iopromide, triiodobenzoic acid, erythrosine and ioversol.

In various embodiments of the invention, a catalyst is used in reactions between a natural polymer and an iodinated compound. A catalyst is a compound capable of assisting in formation of a chemical bond between the natural polymer or protein and iodinated compound. The catalyst may be an organic or inorganic compound or an enzyme and is preferably water soluble. The preferred catalyst is a synthetic organic compound that promotes an ester, amide or urethane bond formation between protein and iodinated compounds. Catalyst that promotes a hydrolyzable bond formation, such as ester, lactone, lactam, disulfide, thioester bond formation, is even more preferred. A catalyst that does not get chemically bonded to the cross-linked/modified natural polymer is even more preferred. This is generally known as "zero length cross-linking" in the protein modification chemistry art. The preferred catalyst of this invention is a class of compounds generally known as carbodiimides. Carbodiimides have following general structure:

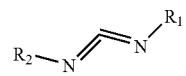

Carbodiimides generally promote reaction between carboxylic acid or amine and hydroxyl groups to form ester or amide bond respectively. Water soluble carbodiimides are most preferred. Water soluble carbodiimide such as 1-ethyl-3-(3-dimethylaminopropyl carbodiimide) hydrochloride (EDC) is most preferred. Other carbodiimides that can be used include but not limited to: 1-(3-dimethylaminopropyl)-3-ethylcarbodiimide methiodide; 1-(3-dimethylaminopropyl)-3-ethylcarbodiimide; 1-cyclohexyl-3-(2-morpholinoethyl) carbodiimide metho-p-toluenesulfonate; 1-(3-dimethylaminopropyl)-3-ethylcarbodiimide and the like. EDC can catalyze a reaction in water over a wide pH range. The pH range may vary from 1 to 9. Most preferred pH range is 5 to 7. The desired pH may be achieved by using a biocompatible buffering agents. The preferred buffers that can be used include, but not limited to, phosphate buffered saline (PBS) (pH 7 to 7.5), morpholino ethanesulfonic acid (MES) (pH 5.5 to 6.5) and triethanol amine buffer (pH 7 to 7.5), sodium acetate buffer and the like. A buffer concentration in the range of 10 mM to 100 mM is preferred. Among the buffers, PBS or MES buffers are most preferred.

In one embodiment of the invention, a co-catalyst that may accelerate the reaction between carbodiimide and iodinated derivative, is added. Examples of such co-catalyst include, but not limited to, n-hydroxysuccinimide or n-hydroxysulfosuccinimide. The molar concentration of co-catalyst is in the same range as that of iodinated compound being reacted. The cross-linking reaction is generally completed with in 1 to 600 minutes, more preferably between 1 to 30 minutes. The preferred reaction temperature is 0 to 45° C. Reaction at 4 to 37° C. temperature range is even more preferred. If necessary, additives that control the properties of modified polymer, such as plasticizers, coloring agents and viscosity modifying, agents, and fillers such as calcium appetite that do interfere with the polymer modification reaction may be added.

The biodegradation of protein based cross-linked gels such as albumin or collagen based gels occurs by an enzymatic pathway. If necessary, the naturally occurring proteases enzymes such as trypsin, collagenases, pepsin and the like may be added during cross-linking and/or iodine modification reaction. A bioactive compound may be added before the modification reaction, or are loaded via diffusion process inside the modified/cross-linked natural polymer.

The reaction conditions such as concentration, temperature, pH are controlled to obtain a desired iodine content in the cross-linked/modified polymer network. In various embodiments of the invention, the desired iodine content of the modified polymer is adjusted to provide sufficient contrast in medical X-ray imaging apparatus. Alternatively two or more iodinated compounds may be used to achieve a desired iodine level. For example, Iopamidol, which has only hydroxy functional groups is used to modify acid functional groups in albumin. Acid functionality of 3,5-bis(acetylamino)-2,4,6-triiodobenzoic acid is used to modify amine functional groups in the albumin. The concentration of total organic iodine in the modified polymer suitable for X-ray imaging range may range from 30 mg/g to 300 mg/g of dry cross-linked polymer. The most preferred iodine concentration range is 50 mg/g to 200 mg/g of dry cross-linked polymer. Even more preferred range is 50 to 150 mg/g of dry cross-linked polymer.

In one exemplary approach, 330 mg of bovine serum albumin was weighed and transferred in 50 ml polypropylene centrifuge tube. 2 ml iopamidol solution (300 mg/g of iodine, Isovue-300 X-ray contrast agent) was added to the tube and was transferred to refrigerator for complete dissolution of albumin in the iopamidol solution. To this solution, 0.2 g n-hydroxysuccinimide and 0.336 g 1-ethyl-3-(3-dimethylaminopropyl carbodiimide) hydrochloride (EDC) were added. After complete dissolution, the reaction mixture was transferred to a refrigerator. After 48 hours, the solution transformed into cross-linked hydrogel. The hydrogel was washed with 10 ml phosphate buffered solution 2 times to remove unreacted reactants from the cross-linked gel. The gel was subjected to x-ray imaging. The albumin hydrogel was clearly visible in developed X-ray film.

Figure 5:
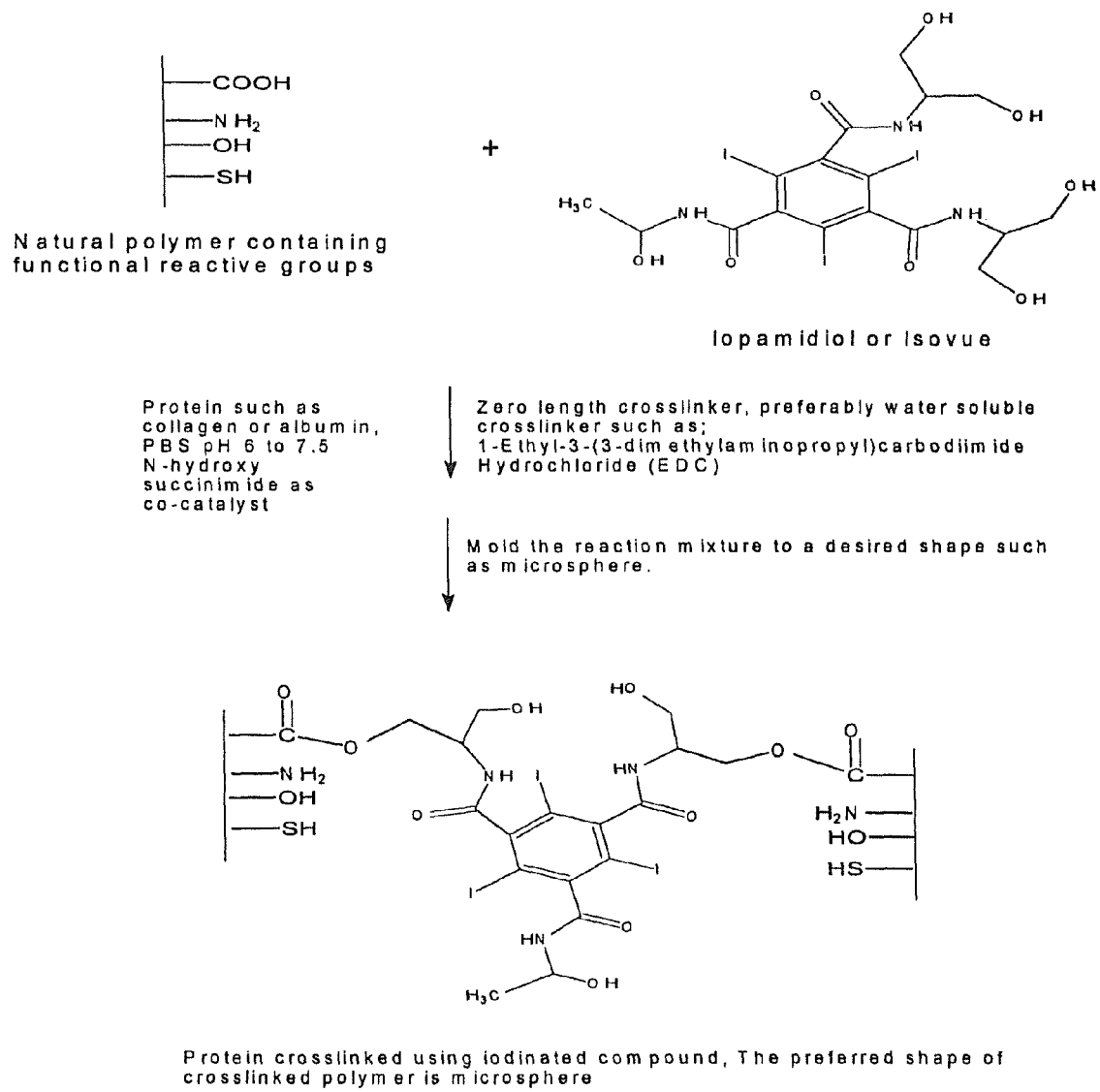
FIG. 5 illustrates an exemplary embodiment in which albumin is reacted with iopamide in presence of EDC and n-hydroxysuccinimide (NHS) as a catalyst.

In some embodiments, the activation of hydroxy group and modification/cross-linking is done simultaneously. FIG. 5 illustrates one exemplary embodiment in which albumin was reacted with iopamide in presence of EDC as a catalyst and n-hydroxysuccinimide (NHS) as a co-catalyst. EDC promotes cross-linking of albumin as well as coupling of iopamidol Ito the albumin. The reaction is carried out in a MES or a PBS buffer for 4-24 hours at PH 5.5 to 7.5. The gel is washed to with a PBS buffer to remove unreacted iopamidol from the cross-linked gel. The reaction variables such as time, temperature, concentration, and pressure are controlled in such a way that 1 to 100 percent primary amine groups and/or acid groups on the protein are modified. More preferably, 10 to 95 percent reactive groups are modified, even more preferably 40 to 95 percent reactive groups are modified. The cross-linked or modified protein is washed to remove soluble unreacted fragments and may be used for implantation or as an absorbable biopsy marker.

In another embodiment of the invention, hyaluronic acid based radio-opaque compositions is made by dissolving hyaluronic acid in Isovue-300 (Iopamidol solution with 30% organically bound iodine) solution at 1-3% concentration. The esterification reaction between hydroxy group of Iopamidol in Isovue and acid group of hyaluronic acid is promoted by the use of EDC as catalyst and n-hydroxysuccinimide as co-catalyst. The radio-opaque hyaluronic acid solution may be used in applications where hyaluronic acid solutions are used. For example, radio-opaque hyaluronic acid may be more useful in accurate placement of the hyaluronic acid when injected between the knee joints.

In another embodiment of the invention, amine groups of chitosan are reacted with 3,5-bis(acetylamino)-2,4,6-triiodobenzoic acid using EDC as a water soluble catalyst and n-hydroxysuccinimide as co-catalyst.

It will be obvious to a person skilled in the art that collagen and gelatin may be modified using a similar reaction conditions as albumin. In one exemplary approach, bovine pericardial tissue that contains collagen as its main constituent, elastin, and glycosaminoglycans is modified using EDC and iodinated compound. Ten pericardium pieces, cut from a freshly obtained bovine pericardial sac, are reacted in 100 mM MES buffer(pH 6.5), with 3,5-bis(acetylamino)-2,4,6-triiodobenzoic acid, iopamidol, EDC and n-hydroxysuccinimide for 48 hours. For additional iodine incorporation, the tissue is further reacted with Iopamidol solution with 30% organically bound iodine using EDC as catalyst and NHS as cocatalyst. The modified tissue is separated and imaged using x-ray imaging technique. Modified tissue with 30 mg/g to 200 mg/g of iodine relative to dry tissue weight is preferred.

EDC cross-linked natural polymer degrades the iodine modified radio-opaque natural polymer into non-toxic amino acid constituents and iodinated compounds such as Iopamidol with known safety profile. Both the amino acid and iodinated compounds are safely eliminated by the body upon degradation.

In various embodiments of the invention, bioactive compound is added to the radio-opaque natural polymer hydrogel for localized therapeutic treatment. The amount of bioactive compound in the composition may be dependent on local disease being addressed, solubility of compound in the composition and toxicology of the compound. The bioactive compound may be added from 0.1% to 30% w/w of total composition. A range of 1 to 10% is even more preferred. Those skilled in controlled drug delivery art will recognize that many changes could be made to achieve a desirable therapeutically effective dose and release of bioactive compound from the cross-linked radio-opaque natural polymer hydrogel could be made. Such changes are considered to be a part of this invention.

In one embodiment of the invention, 1 gram of radio-opaque albumin hydrogel prepared as described previously is incubated in 10 mg/ml paclitaxel solution dissolved in ethanol for 24 hours. The paclitaxel diffuses inside the radio-opaque hydrogel in 24 hour. The hydrogel is removed from the paclitaxel solution, washed with 10 ml PBS solution 2 times to remove surface bound paclitaxel. Alternatively, paclitaxel could be added and suspended in albumin solution prior to cross-linking reaction. The release of paclitaxel from cross-linked hydrogel is monitored for 7 days by incubating the hydrogel in 3 ml PBS solution at 37° C. and exchanging it periodically with fresh PBS. The concentration of paclitaxel eluted in the PBS solution is analyzed by high performance liquid chromatography. A controlled release of paclitaxel from the cross-linked radio-opaque hydrogel is observed. The release profile of paclitaxel from cross-linked radio-opaque hydrogel may be controlled by changing variables such as paclitaxel concentration, the incubation medium, the cross-linked density of radio-opaque hydrogel, and the like.

In various embodiments of the invention, albumin, EDC, NHS, buffering agent and iodinated compound such as Iopamidol are packaged as a kit and used as injectable cross-linkable radio-opaque formulation. All these constituents may be premixed just prior to surgical procedure or mixed in situ using a multi-lumen device such as multi-lumen catheter and injected using MIS surgical technique. For example, such mixture may serve as injectable biodegradable surgical/breast biopsy marker or drug delivery device.

A prefabricated cross-linked radio-opaque albumin or protein that is porous in nature may be useful as surgical biopsy marker. The porosity may be created by many methods known in the tissue engineering scaffold preparation art. On one exemplary embodiment, a cross-linked albumin hydrogel is prepared by reacting iopamidol and albumin in presence of EDC and n-hydroxysuccinimide in water. The water from the crosslinked hydrogel is removed by lyophilization. The removal of water creates a porosity, which filled with air which makes it visible in ultrasonic imaging technique. Air in the porous structure may be replaced with other biocompatible gases such as oxygen, carbon dioxide and the like. Low boiling liquids which form high vapor pressure at body temperature (37° C.) may also be used. These include compounds like fluorinated hydrocarbon based liquids. The total porosity may vary from 20% to 95% of the volume of the implant, more preferably from 50% to 90% of the implant In another embodiment of the invention, 1 g of gelatin, 1 g of iohexol and optimally a magnetic resonance imaging agent (0.25 g) are dissolved in 20 ml phosphate buffered saline. The mixture is poured into a mold and lyophilized to form a porous gelatin sheet. The porosity of sponge along with its entrapped air provides visibility in ultrasonic imaging apparatus while iohexol and magnetic imaging agent provide visibility in medical x-ray imaging technique and magnetic resonance imaging technique respectively. The sponges is cut into small 5 mm circles and spray coated with polylactide-polyglycolide polymer dissolved in chloroform. The coating is applied from all sides of the foam. Upon evaporation of chloroform, the biodegradable polymer coating is formed on the outside of foam (skin formation). This coating limits the access of water to the imaging agents incorporated in the foam thereby preventing their diffusion from the foam. Upon implantation and subsequent degradation of the outside coating, the gelatin foam and its imaging agents are safely eliminated from the body. The imaging agents in the foam provide visibility in x-ray imaging, magnetic resonance imaging and ultrasonic imaging. This visibility in multiple imaging techniques is useful for many minimally invasive surgical techniques including surgical biopsy.

In another embodiment, ionic contract media such as Diatrizoic acid, sodium salt solution is mixed with cationic polymer such as polylysine or chitosan. The anionic salt forms an ionic bond to the cationic polymer such as chitosan or polylysine. Such ionically bound polymeric media can be used as an injectable biopsy marker or for drug delivery use The mixing of anionic contrast media and cationic polymer may be performed in situ to form a gel in situ.

FIG. 6 illustrates exemplary modification scheme for modification of natural polymer such as albumin or antibody using iodinated compound to produce a substantially non-crosslinked water soluble modified polymer. Activated ester n-hydroxy ester of diatrizoic acid capable of reacting with amino group is protein is prepared by reaction of diatrizoic acid with n-hydroxysuccinimide using dicyclohexylcarbodiimide (DCC) as a catalyst in an organic solvent such as dimethyl formamide. Upon isolation and purification of the ester using column chromatography, it is then used in subsequent reaction with protein. The protein solution such as albumin at concentration of 2 to 20% in phosphate buffer pH 7.2 is reacted with diatrizoic acid NHS ester (2-3 molar excess relative to amine group concentration in albumin) at room temperature for 18 hours to form iodinated albumin derivative. The NHS derivative and other small molecular weight compounds are removed by dialysis using 10000 Dalton molecular weight cutoff dialysis membrane. The dialyzed protein solution is lyophilized to isolate the protein.

Radio-Opaque Contrast Media

In various embodiments of the invention, an oligomeric or polymeric polyether chain is linked to a non-polymeric iodinated moiety through a bio stable bond. The radio-opacity of these compounds allows them to be easily traced within the human or animal body thereby enabling their use as contrast media in medical imaging and for localized drug delivery applications.

Figure 7:
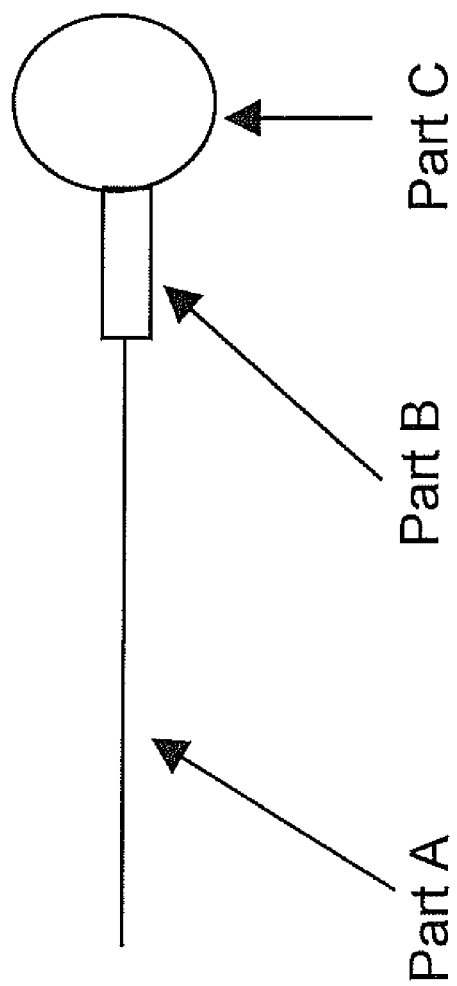
FIG. 7 is a schematic partial representation of radio opaque compound with three parts.

FIG. 7 shows the three structural components of the disclosed radio-opaque compound; the first part (part A) comprises at least one oligomeric or polymeric polyether chain, the second part (part B) comprises at least one non-polymeric iodinated moiety and the third part (part C) comprises one or more hydrolytically stable chemical bond linking part A and part B. The chemical bonds in the three parts are stable when stored in an aqueous environment. In various embodiments of the invention, the combined molecular weight of the three parts of the compound is within 400-30000 Daltons range, more precisely it is between 1000 to 20000 Daltons range and even more precisely in the range of 2000 to 18000 Daltons. In addition, the solubility of the disclosed compounds is at least 1 g/100 ml in an aqueous solution. Typically water solubility of above 1% is believed to be most useful to remove the compound safely from the body. In various embodiment of the invention, the radio-opaque compound is in a liquid state in a temperature range of 10° C. to 45° C.

Figure 8:
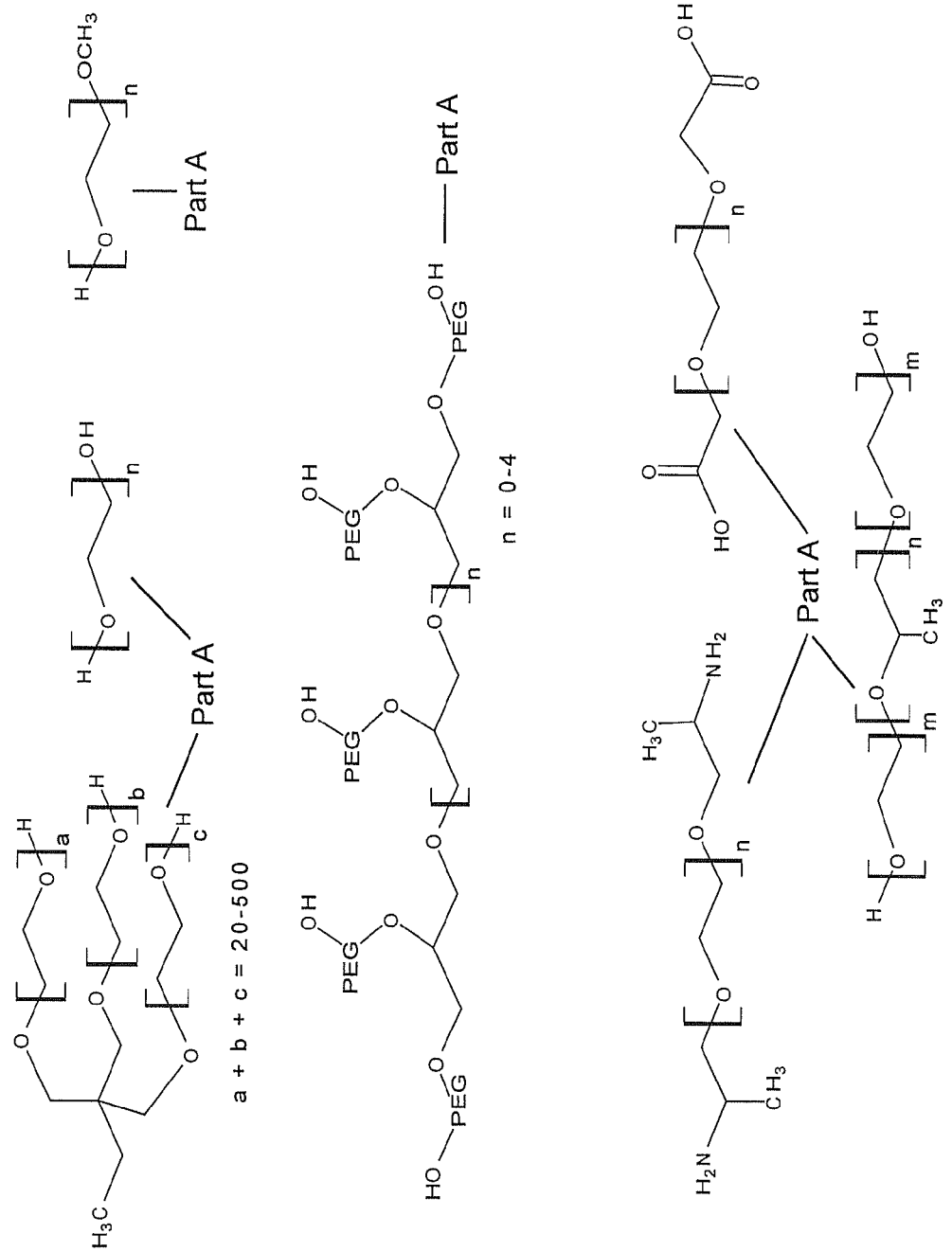
FIG. 8 illustrates exemplary structures that form part A of the radio opaque compound.

FIG. 8 illustrates exemplary structures that form part A of the radio-opaque compound. In various embodiments of the invention, Part A is a polyether oligomer or polymer, such as polyethylene glycol (PEG), polyethylene oxide (PEO), or polypropylene oxide (PPO), polyethylene oxide-polypropylene oxide-polyethylene oxide block copolymer, polypropylene oxide-polyethyleneoxide-polypropylene block copolymer, or a derivative of such compounds. Further, the polyether region of Part A may be a single chain or a combination of multiple chains linked through a chemical bond to the iodinated moiety (part B). Part A may have one or more terminal groups. For example, the polyether chain may be linear with two terminal group, or may be branched, star or dendramer with more than two terminal groups. The molecular weight of part A is in the range of 400 to 20000 Daltons. Molecular weight below 400 makes the radio-opaque compound substantially insoluble in water and renders the compound unsuitable for a number of medical applications. In addition, molecular weight above 20000 Daltons is also not suitable because such high molecular weight makes the compound difficult to remove from the human body. The polyether chain contains at least 70% PEG or PEO by weight. Other polyethers such as polypropylene glycol are insoluble in water at body temperature. PEG content of above 70% makes it soluble in water. In case of multiple chains, the combined molecular weight range of the polyether chain is within a range of 400 to 20000 Daltons.

Figure 9:
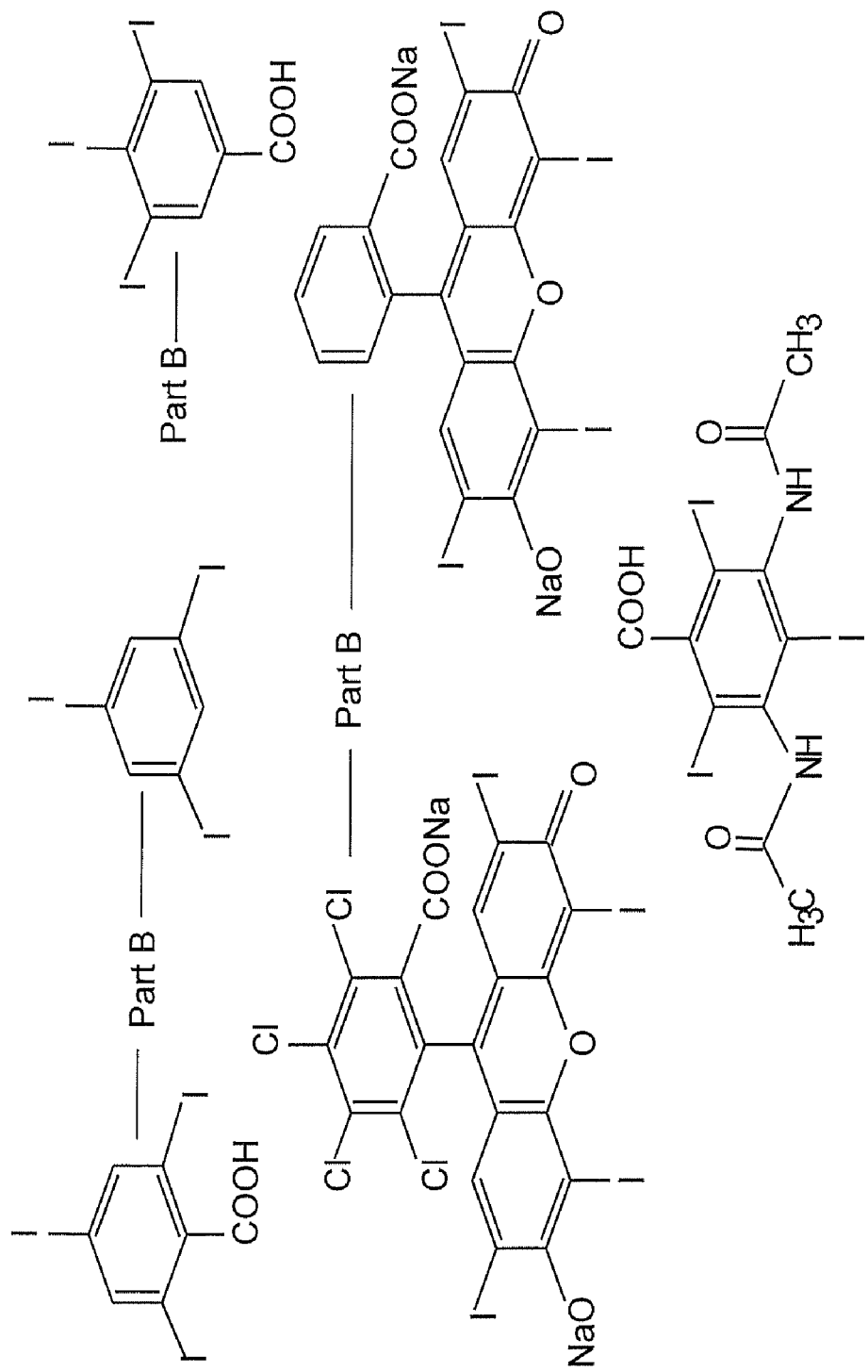
FIG. 9 illustrates exemplary structures that form part B of the radio opaque compound disclosed in the invention.

FIG. 9 illustrates exemplary structures of part B of the radio-opaque compound disclosed in the invention. In various embodiments of the invention, the iodinated moiety is a low molecular weight non-polymeric iodinated compound/radical. Examples of such compounds include substituted benzene ring compounds like triiodobenzene, 1,2,3-triodobenzoic acid, 2,4,5-triodobenzoic acid, triiodobenzyl alcohol, 3-aminotriodobenzene, iodinated xanthene derivatives such as Rose Bengal, Erythrosine and their derivatives. In various embodiments of the invention, the iodinated moiety is non-ionic. The non-ionic nature of the iodinated moiety does not change osmolarity of aqueous solutions of the radio-opaque compound.

Figure 10:
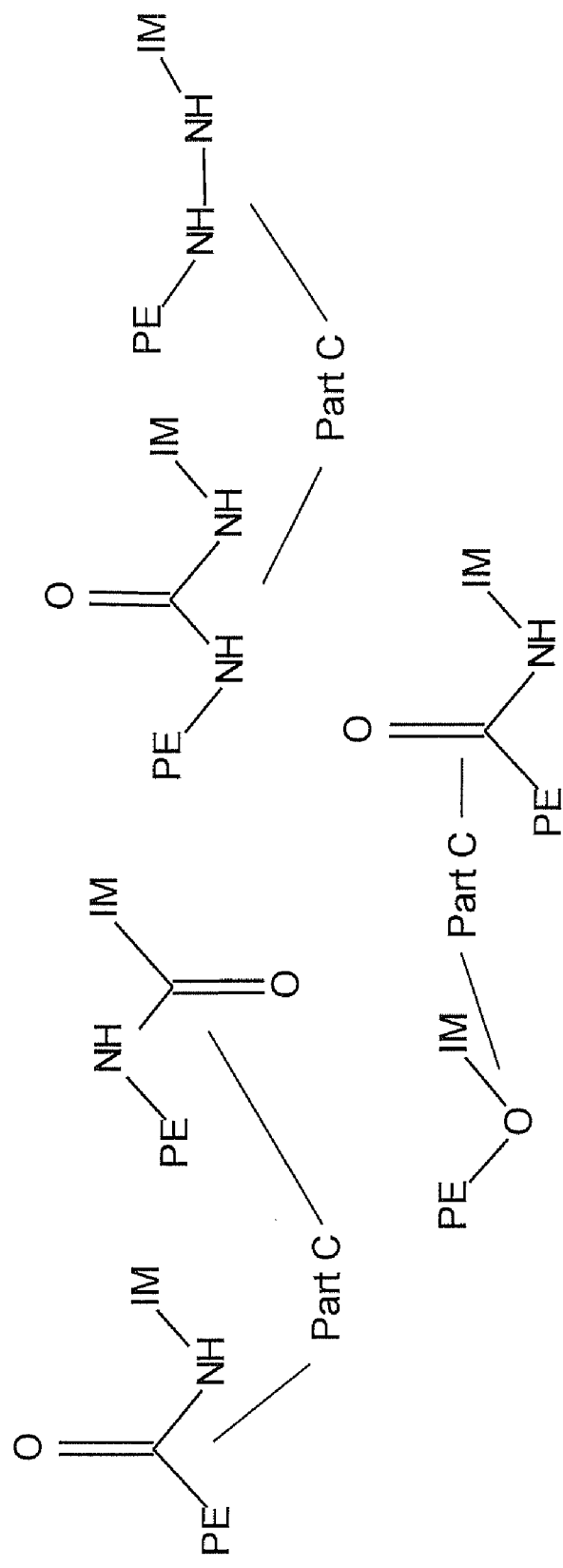
FIG. 10 illustrates examples of hydrolytically stable chemical bonds (part C) of the radio opaque compound disclosed in the invention.

FIG. 10 illustrates examples of hydrolytically stable chemical bonds (part C) of the radio-opaque compound disclosed in the invention. In various embodiments of the invention, the iodinated moiety (IM) is linked to the polymeric chain (PE) by a hydrolytically stable chemical bond. Examples of such hydrolytically stable bonds include: carbon-carbon, carbon-oxygen (ether) and carbon-nitrogen (amide), and carbon-sulfur bonds. Ester and urethane bonds are least preferred due to their hydrolytic instability in an aqueous environment.

Example: In various embodiments of the invention, PEG based radio-opaque compounds with degradable ester links are synthesized. In another embodiment, the compound showed significant degradation (loss of iodine moieties) with 60 day incubation. The stability of the compound was monitored in PBS (pH 7.2) at 37° C. for 30 days. The terminal iodine groups were analyzed by UV spectrophotometer. Therefore polyethylene glycol based radio-opaque compounds containing ester group such as glutarate or succinate are unsuitable for long-term storage in aqueous solutions.

Figure 11:
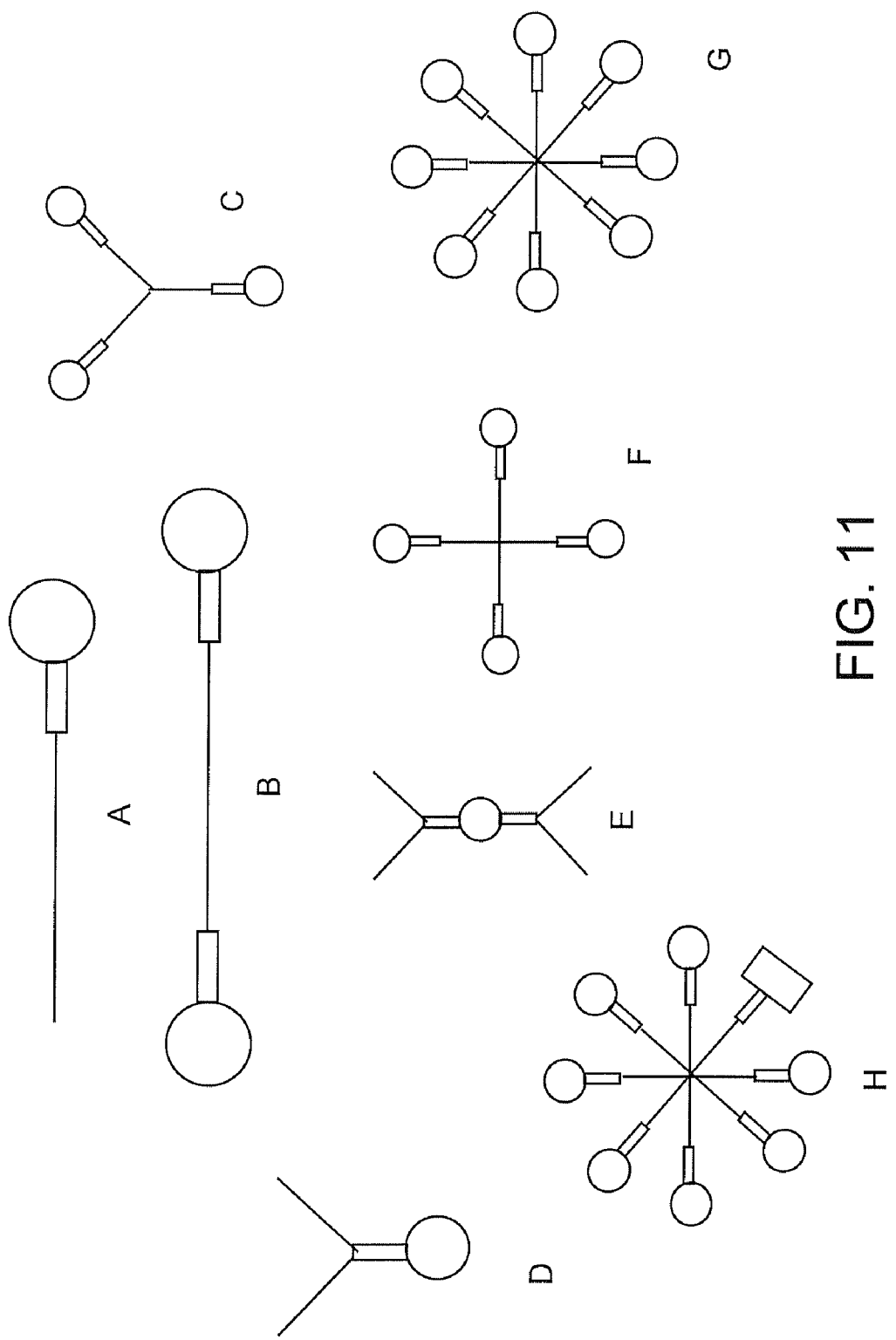
FIG. 11 illustrates exemplary structural arrangements of the radio opaque compounds disclosed in the invention.

FIG. 11 illustrates exemplary structural arrangements of the radio-opaque compounds disclosed in the invention. In various embodiments of the compound, the polymeric chain is terminated with one or more iodinated end-groups. Example A illustrates a linear polyether chain with a single iodinated moiety attached at the terminal end of the chain. B illustrates a linear polyether chain where both the ends are terminated with iodinated moieties. C illustrates a three-arm polyether chain whose ends are terminated with iodinated moiety. D and E illustrate compounds where one iodinated moiety is linked to two and four polyether chain respectively. E and F illustrate 4-arm and 8-arm branched polyether chains respectively, with each arm of the chain terminated with an iodinated moiety. H illustrates an 8-arm polyether chain where only seven ends of the polyether chain are terminated with iodinated moieties and one end is terminated with other moieties. Examples of such moieties include compounds that may be useful in MRI imaging such as ligands containing gadolinium atoms or an antibody that may help to accumulate the radio-opaque compound in an antibody-specific tissue.

Different structural arrangements of the radio-opaque compounds result in compounds with different physical properties such as water solubility, iodine content, melting point, and viscosity. Table 2 describes properties of some compositions.

TABLE 2

Properties of polyether based contrast agents

| Code | Polyether (PE) | Avg. Mol. wt. of PE | Iodinated Moiety | Linking Group | No. of end-groups modified | Iodine atoms per molecule | Iodine (%) |
|---|---|---|---|---|---|---|---|
| P101 | PEG 400 | 400 | Triiodobenzoic acid | Ester | 2 | 6 | 56 |
| P102 | PEG 600 diacid | 400 | Triodophenol | Ester | 2 | 6 | 50.6 |
| P103 | PEG 1000 | 1000 | Triodophenol | Ether | 1 | 3 | 27 |
| P105 | PEG 1000 triol | 1000 | Triiodobenzoic acid | Ester | 3 | 9 | 47 |
| P104 | PEG 1000 | 1000 | Erythrosin | Ester | 2 | 8 | 37 |
| P105 | PEG 1000 diol | 1000 | Triiodobenzoic acid | Ester | 2 | 6 | 39 |
| P106 | PEG 2000 monomethoxy | 2000 | Triiodobenzoic acid | Ester | 1 | 3 | 15 |
| P107 | PEG 2000 amine | 2000 | Triiodobenzoic acid | Amide | 2 | 6 | 26 |
| P108 | PEG 10000 8 arm | 10000 | Triiodobenzoic acid | Ester | 8 | 24 | 22 |
| P109 | PEG 20000 8 arm amine | 20000 | Triiodobenzoic acid | Amide | 8 | 24 | 13 |
| P110 | Pluronic F68 | 8000 | Triiodobenzoic acid | Ester | 2 | 6 | 9 |

Star PEG polymers with 8 arms terminated with a triiodobenzene moiety has 24 iodine atoms per molecule and if terminated with erythrosine has 32 iodine atoms per molecule. A large concentration of iodine atoms per molecule provides better visibility in medical imaging, and allows the use of less concentrated solutions of the compositions disclosed in medical imaging to obtain images with high resolution.

Different tissues in the human body, based on their chemical composition, scatter/absorb/transmit different amount of X-rays and thereby produce an image in the detector. The radio-opaque compounds of the invention can be infused exogenously such that it gets distributed in the tissues to be imaged. The infused compound preferentially absorbs x-rays in the tissue and therefore improves quality of the image. Such improved image results in better diagnosis of the medical condition. Such compounds that help in imaging of tissues are better known as contrast agents.

Figure 12:
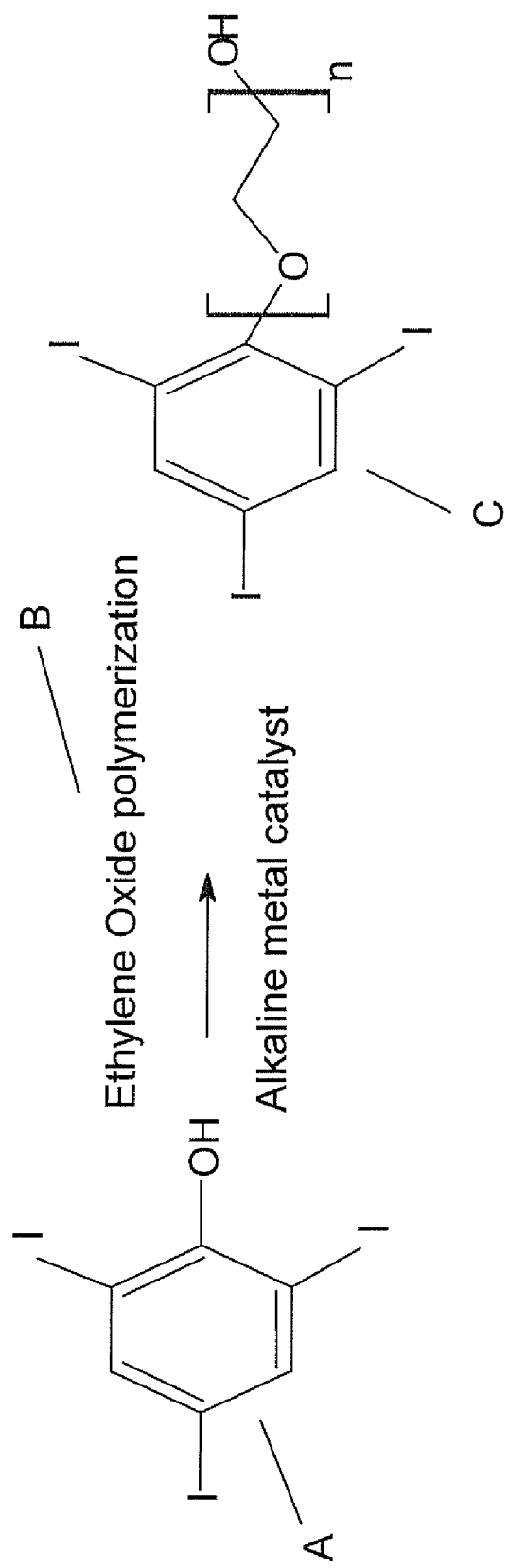
FIG. 12 illustrates an exemplary method for synthesis of the radio opaque compound provided by the invention.

In various embodiments the radio-opaque compounds provided by the invention can be synthesized by different synthetic methods known in the polyethylene glycol modification chemistry art. FIG. 12 illustrates an exemplary method for synthesis of the radio-opaque compound provided by the invention. The example shows synthesis of a compound having one end of the polyether chain terminated with an iodinated moiety. Triiodophenol (A) is used to initiate the polymerization of ethylene oxide (B) using organometallic catalyst to obtain a linear PEG based radio-opaque compound (C). This is a typical ethoxylation modification of alcohol group known in the ethylene oxide polymerization art. The molecular weight of PEG is limited to 1000 Daltons by controlling the molar ratio of ethylene oxide to phenol ratio (molar ratio 22). This molecule has one iodinated moiety per chain and the other chain end is terminated with a hydroxyl group.

Figure 13:
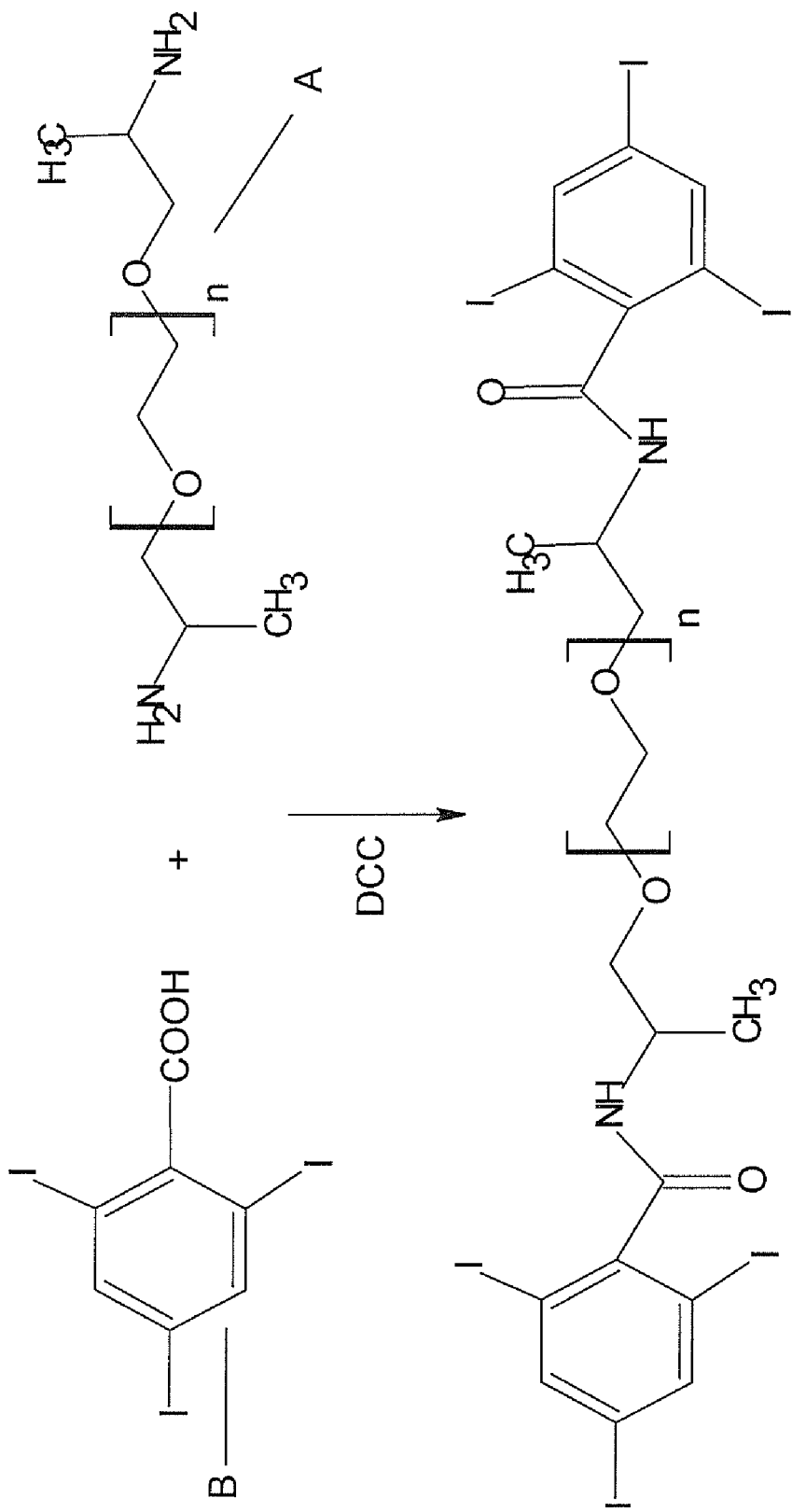
FIG. 13 illustrates an exemplary method for synthesis of radio opaque compound of the invention by modifying the hydroxyl terminal ends of PEG.

FIG. 13 illustrates another exemplary method for synthesis of radio-opaque compound of the invention by modifying the terminal ends of PEG. In various embodiments of the invention the radio-opaque compounds are synthesized by modifying the two terminal ends of commercially available PEG (A), by esterification with triiodobenzoic acid (B). In one embodiment, DCC is used as a catalyst to assist the esterification reaction.

In another embodiment of the invention, a radio-opaque compound is synthesized using a commercially available amine terminated polyethylene glycol (Jeffamine®) and triiodobenzoic acid using DCC as catalyst. The compound has approximately 25% iodine.

In another embodiment of the invention, a radio-opaque compound is an erythrosine terminated polyethylene glycol. Erythrosin has 4 iodine atoms per molecule. Therefore, this molecule has 8 iodine molecules per molecule.

In another embodiment of the invention, an 8 arm amine terminated PEG 20000 is reacted with triiodobenzoic acid to obtain a radio-opaque compound with 24 iodine atoms per PEG chain, linked at each terminal end, through an amide linkage. The amine terminated polymers are available commercially for example Jeffamine can be purchased from Aldrich or from Huntsman Inc. Amine terminated PEG can also be synthesized using methods in the polymer synthesis art.

In another embodiment of the invention, PEG of molecular weight 600 having two terminal hydroxyl groups is reacted with triiodophenol using DCC as a catalyst. The reaction results in a radio-opaque compound with PEG of molecular weight 600 as Part A, triiodobenzene as Part B and an ester linkage as part C. Both the ends of the PEG are substituted with iodinated moiety and the compound is liquid at room temperature.

In various embodiments of the invention, similar ethoxylation chemistry or other known methods of ethylene oxide polymerization known to those skilled in the polymer synthesis art are used to introduce PEG chains on non-ionic iodinated moieties like iohexol, metrizamide, iopamidol, iopentol, iopromide, ioversol by their ethoxylation. The introduction of PEG chains on non-ionic iodinated moieties such as iohexol improves hemocompatibility of such moieties and reduces their interaction with blood proteins. The high molecular weight achieved as a result of ethoxylation is also helpful in reducing number of particles. Increase in molecular weight results into less number of particles in the solution, (lower osmolarity).

In various embodiments of the invention, the terminal end groups of PEG chain after ethoxylation are reacted with functional monomers such as acryloyl chloride or methacryloyl chloride to obtain radio-opaque polymerizable macromonomers. These macromonomers are water soluble due to polyethylene glycol chain and can form radio-opaque hydrogels upon free radical polymerization and cross-linking.

Radio-opaque compounds prepared according to disclosed exemplary methods and their modifications are listed in Table 2 along with their calculated iodine content. As can be seen from this table, compounds with wide range of iodine contents, molecular weights, degree of branching can be synthesized.

In various embodiments of the invention, two different radio-opaque compounds with different molecular weight but same Iodine content are obtained. A linear polyethylene glycol with molecular weight 2000 terminated with triiodibenzoic acid has the same amount of iodine as polyethylene glycol with molecular weight 8000 having 8 arms terminated with triiodobenzoic acid. The radio-opaque compound with high molecular weight polymer (8000) has substantially less number of particles in aqueous solution as compared to the radio-opaque compound with low molecular weight counterpart when dissolved at equal concentration (wt/v). Thus, high molecular weight polymer is useful in reducing osmolarity of the solution of radio-opaque compounds without compromising on the iodine content.

In various embodiments of the invention, compositions of radio-opaque compounds also contain, a buffering agent such as phosphate salts, triethanol amine, HEPES to maintain a pH in the range of 5 to 8, precisely in the range of 7 to 8 and more precisely in the range of 6.8 to 7.5.

Table 3 lists ingredients of an exemplary aqueous compositions for X-ray imaging.

TABLE 3

| Component of composition | Function | Weight (g) |
| --- | --- | --- |
| Jeffamine triiodobenzamide | X-ray absorbing polyether component | 40 |
| Triethanol amine | Buffering Agent | 0.15 |
| Triethanol amine hydrochloride | Buffering Agent | 0.19 |
| Sodium chloride | Osmolarity balancing agent | 0.36 |
| Distilled deionized water | Solvent | 59.30 |

Table 4 lists ingredients of an exemplary aqueous composition comprising polymeric and non-polymeric non-ionic contrast agents.

TABLE 4

| Component | Function | Weight (g) |
|---|---|---|
| Jeffamine triiodobenzamide | X-ray absorbing polymeric component | 28 |
| Iohexol | X-ray absorbing non-ionic component | 43 |
| 20 mM triethanolamine buffer, pH 7.2 | Solvent | 29 |

Since many PEG based synthesis preparations frequently result in loss of antioxidants present in the PEG raw material, the lost antioxidant must re-added in the final formulation to improve shelf life and stability of PEG molecules. In various embodiments of the invention, antioxidants of are added in very small amounts to the composition, typically in the range of 0.0001% to 2% and precisely in the range of 0.005% to 0.1% percent. Examples of antioxidants that are added include butylatedhydroxy toluene (also known as BHT or 2,6-di-tert-butyl-4-methylphenol), butylatedhydroxy anisole (BHA), hydroquinone, vitamin E or any other suitable antioxidants known in the pharmaceutical dosage preparation art.

Concentrated aqueous solutions of PEG containing compositions described in this invention may have tendency to form foam during routine handling of the solution. In various embodiments of the inventions, defoaming agents are added; to reduce the amount of foam formation. Examples of such defoaming agents include fatty acid alcohols, aliphatic long chain alcohols, octanol, 1,2-octanediol, decanol, silicone fluids etc. The antifoaming agents are added in the range of 0.0001 to 2%, more precisely in the range of 0.001 to 0.1%.

Table 5 provides exemplary aqueous compositions for X-ray imaging comprising antioxidant, de-foaming agent, and viscosity reducing agent.

TABLE 5

| Component | Function | Weight (g) |
|---|---|---|
| Jeffamine triiodobenzamide | X-ray absorbing polyether component | 32 |
| Triethanol amine | Buffering Agent | 0.15 |
| Triethanol amine hydrochloride | Buffering Agent | 0.19 |
| Sodium chloride | Osmolarity balancing agent | 0.36 |
| Distilled deionized water | Solvent | 67.3 |
| 1-octanol | De-foaming agent | 0.02 |
| BHT | Antioxidant | 0.005 |
| Ethanol | Viscosity reducing agent | 8 |

Figure 14:
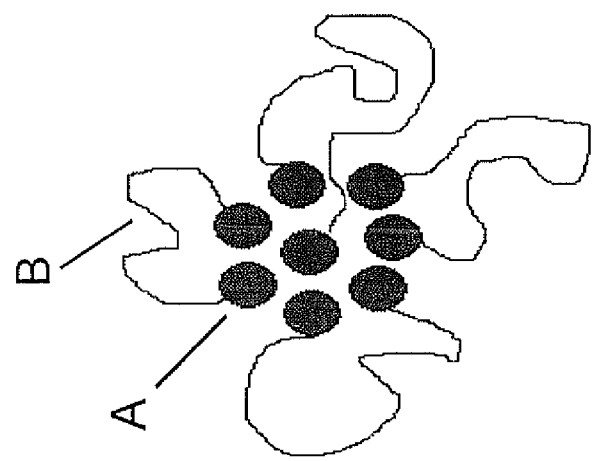
FIG. 14 illustrates self-assembly property of the radio opaque compounds in aqueous medium.
Figure 14:
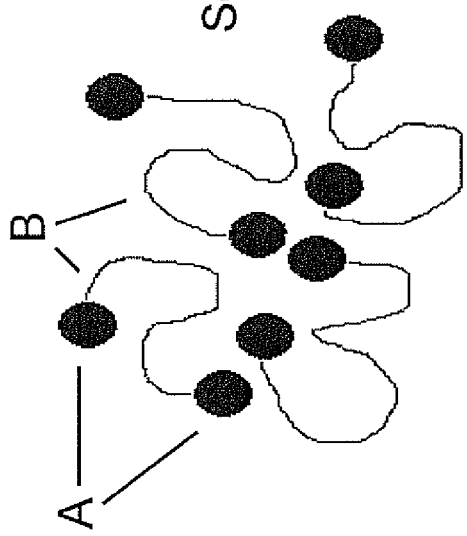

FIG. 14 illustrates the self-assembly property of the radio-opaque compounds in aqueous medium. In various embodiments of the invention, the iodinated moieties (A) linked to polyether chain (B) self assemble in an aqueous environment. The formation of iodine rich hydrophobic domains in water leads to localized high concentrations of iodine providing better contrasting properties at low iodine concentration. The carbon-oxygen bond in PEG or polyether chain permits free rotation along the carbon-oxygen axis. In aqueous environment, the rotational flexibility permits the polyether chain ends to retain mobility.

In an embodiment of the invention where the iodinated moiety is triiodobenzene, the planar structure of triiodobenzene ring and its high hydrophobicity results in iodine rich hydrophobic domains when dissolved at high concentrations in water, typically above 0.1% percent wt/v. Such domains have very high iodine content (as the iodine content of triiodobenzene ring is 84 percent) and attenuate the x-rays with high efficiency, thereby improving contrast properties in medical x-ray application.

The contrast media compositions described in various embodiments of the invention can be used for medical imaging applications. The list of such applications includes but is not limited to: intravascular use; angiography, urography, phlebography and CT-enhancement; subarachnoid use: lumbar, thoracic and cervical myelography and in computed tomography of the basal cisterns; body cavities: arthrography, endoscopic retrograde cholangiopancreatography (ERCP) and pancreatography (ERP), herniography, hysterosalpingography and sialography.

The radio-opaque compounds described above can be combined with physiologically acceptable carrier media to form various contrast agent compositions and pharmaceutical compositions.

The pharmaceutical compositions can be used for localized drug delivery applications. Such compositions contain a bioactive compound dissolved in the hydrophobic domains of radio-opaque compound. The bioactive compounds can be released in a controlled manner in human or animal body.

The formation of self-assembly largely depends on temperature, pH, carrier medium, molecular structure (terminal versus non-terminal), type of iodinated moiety and molecular weight of PEG chain.

Compositions self assembled between 15-45° C., more preferably between 25 to 37° C. are preferred. Self assembly in aqueous environment such physiological pH 7.2 is even more preferred. It is recognized that self assembly property is very specific to carrier used and organic solvents such as chloroform are not useful for self assembly formation and therefore cannot be used. For self assembly, PEG molecular weight between 600 to 30000 Daltons per IM moiety is preferred; PEG with molecular weight 1000 to 20000 Daltons is even more preferred.

In various embodiments of the invention, the self-assembly is further assisted by adding hydrophobic compounds to the aqueous solution of radio-opaque compounds. Example of such hydrophobic compounds include long chain alcohols, naturally occurring fatty acids, triiodobenzoic acid, Erythrosin, iohexol, metrizamide, iopamidol, iopentol, iopromide, and Ioversol, octanol, 1-8-octanediol, 1,2-octanediol, oleic acid, steric acid, vitamin E, vitamin E acetate, and vitamin E modified with polyethylene glycol.

In various embodiments of the invention, the hydrophobic compounds are bioactive compound such as paclitaxel or Lovastatin. These compounds are added in various proportions depending on their solubility, iodine content and toxicological profile. Such compounds are added precisely in the range of 0.1% to 70% range, more precisely in the range of 1 to 50%, even more precisely in the range of 5 to 30%.

In various embodiments of the invention, the self-assembly behavior of these radio-opaque compounds is exploited to deliver bioactive compounds (dissolved in the hydrophobic domains) in human or animal body. The bioactive compounds are released in a controlled manner. In one embodiment, paclitaxel dissolved in ethanol is added to 30 percent aqueous solution of PEG 8-arm triiodobenzamide. The solution is filtered to remove unsolubilized paclitaxel. The paclitaxel dissolved composition is used as a contrast agent as well as a controlled drug delivery vehicle. In another embodiment, such composition is used to deliver paclitaxel at the site of angioplasty to control restenosis.

In various embodiments of the invention, ionic and non-ionic compositions of radio-opaque compounds with 50-500 mg I/g Iodine content, more precisely 140-400 mg I/g are used in medical x-ray imaging.

In various embodiments of the invention, some compositions containing the radio-opaque compounds exist as neat liquids, which may be directly injected and used as contrast agents. Liquids have an advantage over solutions that they can be used without any solvent such as water. Water is also a reactive solvent and can cause hydrolysis of the contrast agent. Elimination of water can improve storage stability. Since pure liquids do not have any solvent, they also can have high iodine content that results into better x-ray image quality. Liquids also can be filter sterilized which can simplify manufacturing process. Removal of solvents/water from formulation also reduces the osmolarity of the final formulation as the dissociation of molecules in water results into high osmolarity.

In various embodiments of the invention, the compositions existing as neat liquids are used as solvents for ionic/non-ionic contrast media compounds or for bioactive compounds. Examples of such compounds include Iohexol, Metrizamide, iopamidol, iopentol, iopromide, triiodobenzoic acid, Erythrosin and Ioversol. These compounds are mixed with the compositions of the invention in the range of 0.1 to 90 percent, precisely in the range of 1 to 30 percent. Various properties of these compositions (such as percent iodine content, viscosity, cost) can be controlled by adding mixtures. Examples of such mixtures include organic buffering agents such as triethanol amine, HEPES, and viscosity controlling agents such as ethanol, polyethylene glycol, glycerol, 1,2-propane diol, 1,4-octanediol, 1-5 pentane diol, isopropanol, n-methyl pyrrolidinone and dimethyl sulfoxide.

Table 6 describes one such example of a contrast agent dissolved in a neat liquid composition containing the radio-opaque compound.

TABLE 6

| Component | Function | Weight (g) |
|---|---|---|
| PEG 1000 triiodobenzamide | X-ray absorbing polyether component | 85 |
| Ethanol | Viscosity modifier | 15 |

In various embodiments of the invention, ionic or non-ionic iodinated contrast media compounds used in current clinical practice such as iohexol, metrizamide, iopamidol, iopentol, iopromide, and Ioversol are mixed with commercially available biostable biocompatible polymers such as polymers used in fabrication of long term (typically more than six months) implantable medical devices to obtain a polymer. Examples of polymers used in fabrication of long term implantable medical devices include polyesters such as polyethylene terephthalate, polyethylene, polyurethanes such as polycarbonate polyurethanes, polyether polyurethanes, polytetrafluoroethylene (Teflon), polypropylene, polymethacrylates such as polymethyl methacrylate or polybutyl methacrylates, ethylene vinyl acetate copolymer or their derivatives, fixed animal tissues such as glutaraldehyde fixed tissue, silicone rubber and the like. The blending can be carried out using variety of technique known in the polymer/rubber processing art such as solvent based methods, melt based methods.

In various embodiments of the invention, compositions containing ionic and non-ionic contrast agents such Metrizamide, iopamidol, iopentol, iopromide, and Ioversol in non-aqueous medium are disclosed. The non-aqueous medium offers a unique way to control ionization of contrast agents. Use of non-aqueous organic medium prevents ionization therefore eliminating side effects associated with the ionization. Another advantage of organic solvents is that they may permit the use of contrast agents that are unstable in aqueous solutions. 1 to 90 percent solutions of Metrizamide, iopamidol, iopentol, iopromide, and Ioversol in biocompatible organic solvents are used. Examples of non-aqueous solvents that can be used are polar solvents like n-methyl pyrrolidinone, dimethyl sulfoxide; alcohols such as ethanol, isopropanol, 1,3-propane diol, 1,4-butane diol, glycerol; polyethylene glycol and fatty acids such as oleic acid. A mixture of these solvents in any proportion may be used. In some cases water can be used as a cosolvent.

Table 7 lists ingredients of an exemplary non-aqueous based contrast media composition.

TABLE 7

| Component | Function | Weight (g) |
|---|---|---|
| PEG 1000 tribenzoacetamide | X-ray absorbing polyether component | 80 |
| Ethanol | Non-aqueous solvent | 10 |
| N-methyl pyrrolidinone | Non-aqueous solvent | 10 |

In another embodiment of the invention, iodinated compound such as Iohexol or 3,5-Diacetamido-2,4,6-triiodobenzoic acid and high molecular weight ethylene vinyl acetate copolymer//butyl methacrylate copolymer are mixed in the organic solvent such as dimethyl sulfoxide or chloroform. The solvent is removed to form a film. The polymeric film is radio-opaque when viewed using medical x-ray imaging equipment. Since many biocompatible polymers such as polyesters, polyethylene, polyurethanes, polytetrafluoroethylene (Teflon), polypropylene, polymethyl methacrylate, ethylene vinyl acetate copolymer, silicone rubber and Iohexol have proven history of human use, the devices will face relatively less regulatory scrutiny. Alternately, iodinated compositions described in this invention may also be physically mixed or blended to produce a radio-opaque biostable device.

The iodinated compound physically mixed with the biodegradable or biostable polymer may be completely soluble in the polymer matrix or may exist as separate phase. The phase separation will depend on the molecular structure of the polymer and iodinated compound used. In a heterogeneous mixture of iodinated compound and polymer matrix, the iodinated compound size may range from 50 nm to 1000 microns depending on the method of preparation and polymer/iodinated compound molecular structure. The preferred size of iodinated compound in the composite matrix is 0.1 to 200 microns. Alternatively, iodinated compound may be first obtained in a particular size of interest and then dispersed in the polymer matrix. Many methods known in the drug delivery dosage preparation art may be used to prepare an iodinated compound of particular size. In one exemplary method, commercially available iodinated compounds such as metrizamide or sodium diatrizoate dihydrate may be cryogenically ground and sieved using standard mechanical sieves/meshes. The fraction of particles having a size in between 100 and 200 microns is collected and used in preparing polymer-iodinated compound mixture. The iodinated compound particle shape may be spherical, cylindrical, cubical, irregular and the like.

Some of the biodegradable and biostable radio-opaque compositions described in this invention may be optically transparent or semi-transparent (transparent in the visible spectrum of light from 400 to 800 nm) due to solubility of iodinated compound in the polymer matrix and the transparent nature of polymer used. Such compositions may be useful to form transparent and radio-opaque medical devices such as angioplasty catheters or as transparent and radio-opaque coatings for medical devices. Polyurethane, polylactones and acrylic based transparent and radio-opaque compositions and coatings are especially preferred.

In another embodiment of the invention, a non-polymeric liquid carrier such as sucrose acetate is mixed with iodinated compounds such as Metrizamide, iopamidol, iopentol, iopromide, and Ioversol to make it radio-opaque.

Water is not a very good solvent for PEG based compositions described in this invention. Use of non-aqueous compositions is also very useful in controlling viscosity of final composition for medical imaging. Polymeric contrast media generally have high viscosity. This viscosity can be reduced by adding biocompatible organic solvents. When non-aqueous compositions are introduced in the aqueous environment, such as physiological environment, the PEG based compositions may temporarily form water swollen hydrogels that, will dissolve as they are further diluted away. Such temporary gel formation may be helpful in improving contrasting properties at the site of injection.

Thermosensitive Gels

The present invention also provides radio-opaque compositions that undergo gelation due to physical cross-linking and/or change in temperature. In one exemplary embodiment, a block polyether copolymer (Pluronic F127) that shows thermoreversible gelation in water and a water soluble iodinated compound are dissolved in PBS solution. Pluronic F127 is dissolved in commercially available X-ray contrast agent solution to produce a 30% Pluronic F 127 in Isovue solution. When the Pluronic-Isovue solution is cooled to 15° C. or below, the solution is observed to be free flowing and could be injected using a syringe. When the same solution is warmed to body temperature (37° C. or above), it is transformed into a non-fluid hydrogel. The gelled solution may also be injected as a paste. The Pluronic-Isovue solution in fluid state as well as in gel state is visible in X-ray imaging apparatus. In various embodiments of the invention, the Pluronic-Isovue solution may be added with bioactive compound to produce local therapeutic effect. In the present invention polymers that show thermoreversible gelation and that can be used safely inside the body are preferred. The polymers may be biodegradable or bio-inert. The preferred polymers, their derivatives and analogs include, but are not limited to: PEO-PPE-PEO block copolymers (Pluronic surfactants from BASF), PPO-PEO-PEO block copolymers (Reverse Pluronics), Tetronics copolymers: PEO-polylactone-PEO and polylactone-PEO-polylactone block copolymers, PEO-polyhydroxy acid-PEO, polyhydroxyacid-PEO-polyhydroxy acid, PEo-polyhydroxy acid, PEO-polycaprolactone copolymers, gelatin and the like. Some gelatin derivatives and PEO-polylactone-PEO, and polylactone-PEO-polylactone block copolymers show gelation when their warmed aqueous solutions (temperature 37 to 55°) are cooled to body temperature. When aqueous solutions are warmed to 45° C. or above, upon cooling, the solution of these derivatives turns into a non-fluid hydrogel. The concentration of polymer in water will depend on the polymer chosen. For example, polymers like Pluronic F127 show thermoreversible gelation at 10 to 50% concentration range, more preferably 20-30% concentration range. A concentration where polymer shows thermoreversible gelation around body temperature is most preferred.

The iodinated compound provides radio-opacity to the thermoreversible gel. The preferred iodinated compounds are water soluble and with three to four iodine atoms per molecule. The preferred iodine compounds include, but not limited to, iohexol, metrizamide, iopamidol, 3,5-bis(acetylamino)-2,4,6-triiodobenzoic acid, meglumine diatrizoate, iopentol, iopromide, triiodobenzoic acid, erythrosine and ioversol and their derivatives. The iodinated compound is added in sufficient amount to produce a good quality image in medical X-ray image apparatus. The preferred amount of organically bound iodine in the solution or gel may range from 3 percent to 40 percent, more preferably 10 to 20 percent. The amount of iodine used may vary depending on the medical X-ray imaging technology used. The newer machines with better detector need small amount of iodine content to form a good image. Additional additives such as biocompatible coloring agent may be added to the compositions described above to improve visibility during open surgery. In addition, an antioxidant may be added to improve shelf life and the like.

In various embodiments, the iodinated compounds are chemically bound to the polymer that shows thermoreversible gelation. In one exemplary embodiment, Pluronic F68 copolymer that shows thermoreversible gelation is reacted with triiodobenzoic benzoic acid using DCC as a catalyst. The modified polymer isolated and redissolved in water to form aqueous solution. Concentrated aqueous solution of triiodo ester of Pluronic F127 (typical concentration >20%) display thermosensitive gelation behavior. In addition, additional iodine containing compounds mentioned above may be added to increase iodine content of the polymer.

In various embodiments of the invention, bioactive compounds are be added to the thermosensitive composition for local therapeutic effect. The amount of bioactive compound in the composition may be dependent on local disease being addressed, solubility of compound in the composition and toxicology of the compound. The bioactive compound may be added from 0.1% to 30% w/w of total composition. A range of 1 to 10% is even more preferred.

The biodegradable radio-opaque composition of the invention may be formulated such that it can be delivered using with Minimally Invasive Surgical (MIS) techniques. Examples of such techniques include, but are not limited to laparoscopy, thoroscopy and simple injection.

Such molded or tissue conformed polymers are applicable for medical conditions where a temporary presence of biocompatible, biodegradable polymeric devise is desired. Exemplary applications include, but are not limited to prevention of postoperative adhesions, prevention of scar formation after laminectomy and the like Hydrophobic Radio-Opaque Biodegradable Compositions This invention also provides methods and compositions for making injectable hydrophobic radio-opaque biodegradable compositions.

In various embodiments, iodinated compounds such as ionic and non-ionic contrast agents are mixed or blended with commercially available polymers such polylactones and polyhydroxyacids, and the biodegradable radio-opaque compound of the present invention. These ionic and non-ionic contrast agents are used as a filler in biodegradable polymers. Examples of ionic and non-ionic contrast agents include, but are not limited to triiodobenzoic acid, meglumine diatrizoate, diatrizoic acid salts, metrizamide, iopamidol, iopentol, iopromide, and Ioversol. Typically, iodinated compounds are added in 1 to 90% range more typically from 5 to 70% weight range.

In another embodiment of the invention, biodegradable polymer and an iodinated compound are mixed with biocompatible organic solvent such as n-methyl pyrrolidinone or dimethyl sulfoxide. The mixture is transported to a surgical site and deposited inside the human body. The presence of iodinated compound makes the composition visible under x-ray imaging equipment.

In another embodiment of the invention iodinated compound such as Iohexol and high molecular weight polyhydroxy acid or polylactide copolymers are mixed in the organic solvent such as dimethyl sulfoxide. The solvent is removed to form a polymeric film. The polymeric film is radio-opaque when viewed using medical X-ray imaging equipment.

In another embodiment of the invention, the low melting triiodobenzoic acid terminated polymer and an antibiotic such as tetracycline is deposited as a melt inside a periodontal cavity. The polymer solidifies inside the periodontal cavity. The drug is then released in a sustained manner over a period of time. The drugs may be incorporated into fine particles such as microspheres of hydrophobically and hydrophillically end-capped biodegradable polymers. Subsequently a dispersion of these microspheres may be injected parenterally, subcutaneously and intramuscularly using suitable surgical technique. It will be apparent to a person skilled in the art that other methods of drugs administration and controlled drug delivery may be envisaged.

In one preferred embodiment, a low melting biodegradable polymer is physically mixed with a water soluble iodinated compound. The mixture is then filled in an MIS delivery device and transported to a surgical site. The mixture is melted 'in-situ' and injected at the implant site to fill a body cavity or void. The mixture solidifies in the body cavity. The iodinated compound that remains entrapped in the biodegradable polymers provides radio-opacity to the solidified implant. Upon degradation, the iodinated compound and the hydrolysis products of biodegradable polymer are safely removed from the body. Biodegradable polymer with molecular weight 400 to 30000 g/mole may be preferred due to their low melt viscosity. Molecular weight between 1000 to 10000 g/mole is even more preferred. The preferred biodegradable polymers that may be used include, but not limited to: polymers, copolymers or oligomers of: glycolide, dl-lactide, d-lactide, l-lactide, caprolactone, dioxanone and trimethylene carbonate or their copolymers; polyhydroxyacids, polyesters, polyorthocarbonates, polyanhydrides, polylactones, polyaminoacids and polyphosphates. Biodegradable polymers suitable for this application must have melting point between 40 to 70° C. Even more preferably, the melting point must be between 40 to 55° C. The preferred polymers or copolymers or their blends and derivatives that can be used in this application include, but not limited to: polycaprolactone, polycaprolactone-polyethylene glycol block copolymers, polyethylene glycol-polyhydroxy acid copolymers, polyethylene glycol-polylactone block copolymers. Polyethylene glycol-polytrimethylene carbonate block copolymers. The polyethylene glycol block copolymers may be AB, ABA or BAB type.

The polymer architecture such as number of branches per molecule may be altered to achieve a suitable melting point. For example, branched or star shaped polymers generally have lower melting points as compared to their linear analogs. A synthesis of low melting polyethylene glycol polylactide block copolymer is shown in one illustrative example. Polymers that generate low melt viscosity are even more preferred.

Iodinated compounds that can be used to provide a radio-opaque property should be safely removed from the human or animal body. The preferred iodinated compounds are water-soluble and have 3 to 4 iodine atoms per molecule. The preferred iodine compounds include, but not limited to: iohexol, metrizamide, iopamidol, 3,5-bis(acetylamino)-2,4,6-triiodobenzoic acid, meglumine diatrizoate, iopentol, iopromide, triiodobenzoic acid, erythrosine and ioversol. The iodinated compound is added in sufficient amount to produce a good quality image in medical X-ray image apparatus. The amount of iodine used may vary depending on the medical X-ray imaging technology used. The newer machines with better detectors or x-ray film may need small amount of iodine content to form a good image. The preferred amount of organically bound iodine in the mixture may range from 5 percent to 40 percent, more preferably 10 to 20 percent.

Additional additives may be added to the compositions described above. These additives may include biocompatible plasticizers that help to reduce the melting point, a biocompatible coloring agent to improve visibility during open surgery, an antioxidant to improve shelf life, a crystallizing agent to improve solidification rate, a biocompatible filler that may improve mechanical properties and the like.

In various embodiments of the invention, bioactive compounds may be added with the radio-opaque compositions described above for local therapeutic effect. The amount of bioactive compound in the composition may be dependent on local disease being addressed, solubility of compound in the composition and toxicology of the compound. The bioactive compound may be added from 0.1% to 40% w/w of total composition. A range of 1 to 10% is even more preferred.

In another embodiment, a bioactive compound such as rifampin is added to the low melting polymer and iodinated compound mixture. The radio-opaque biodegradable composition can be used to release rifampin locally.

In one exemplary approach, 4 g Polycaprolactone (molecular weight 2000 g/mole) and 1.0 gram 3,5-Bis(acetylamino)-2,4,6-triiodobenzoic acid sodium salt are dissolved/suspended in dimethyl sulfoxide. The solvent is removed by vacuum drying at 50° C. for 24 hours. The mixture is then partially filled in 3 ml polypropylene syringe. The syringe is then heated to 70° C. for 1 hour to melt the mixture. The liquid melt can be pushed out using the syringe plunger. The biodegradable polymer and iodinated compound of the above-mentioned example is clearly visible in X-rays.

Some low melting compositions, particularly compositions prepared from polyethylene glycol-polylactone copolymers may absorb water upon injection in the body. The absorption of water in the body may increase the size of the implant. The increased size of the implant may advantageously help the implant to entrap itself with in the tissue cavity. The absorption of water depends on the amount of polyethylene glycol in the copolymer and its molecular weight. Polyethylene glycol with molecular weight 400 to 20000 g/mole is most preferred. The amount of polyethylene glycol in the copolymer may range from 10% to 98% most preferably 40 to 70%. Such polymers may be especially useful as biodegradable surgical/breast biopsy markers.

In some medical applications, it is necessary to use low viscosity liquids and solutions that are radio-opaque and are capable of releasing a bioactive compound in a controlled manner. This invention also provides novel methods and compositions that permit injection of radio-opaque biodegradable polymer solution in a tissue cavity.

In various embodiments of the invention, commercially available synthetic biodegradable polymer is dissolved in biocompatible water miscible solvent. The radio-opacity is achieved by dissolving a biocompatible iodinated compound along with the polymer. In addition, a bioactive compound may be added to achieve a desired therapeutic effect. The solution is then injected in side body or in the tissue cavity. Upon injection, the solvent diffuses out from the mixture, leaving behind the polymeric implant. The radio-opaque compound entrapped in the implant provides radio-opacity, which facilitates monitoring movement and degradation of the composition for a local therapeutic effect.

Hydrophobic biodegradable polymers are preferred for this application. The preferred polymers that can be used include, but not limited to: polymers, copolymers or oligomers or their derivatives or blends of: glycolide, dl-lactide, d-lactide, l-lactide, caprolactone, dioxanone and trimethylene carbonate or their copolymers; polyhydroxyacids, polyorthocarbonates, polyanhydrides, polylactones, polyaminoacids and polyphosphates. Solvents that can be used to dissolve the biodegradable polymer include solvents that are capable of dissolving the polymer and are water soluble and biocompatible. The preferred solvents that can be used include, but not limited to: dimethyl sulfoxide, n-methyl pyrrolidinone, acetone, polyethylene glycol, glycerol, oleic acid, 1,-4 butane diol, propylene glycol, ethanol, ethyl lactate, and the like. Dimethyl sulfoxide and n-methyl pyrrolidinone are preferred due to their ability to dissolve wide variety of biodegradable polymers, iodinated compounds and bioactive compounds. The iodinated compounds are preferably water soluble and have three to 4 iodine atoms per molecule. The preferred iodine compounds include, but not limited to: iohexol, metrizamide, iopamidol, 3,5-bis(acetylamino)-2,4,6-triiodobenzoic acid, meglumine diatrizoate, iopentol, iopromide, triiodobenzoic acid, erythrosine and ioversol. The iodinated compound or compounds is/are added in sufficient amount to produce a good quality image in medical X-ray image apparatus. The amount of iodine used may vary depending on the medical X-ray imaging technology used. The newer machines with better highly sensitive detector may need small amount of iodine content to form a good image. The preferred amount of organically bound iodine in the mixture may range from 3 percent to 40 percent, more preferably from 10 to 20 percent. In addition, additives such biocompatible viscosity modifier that help to reduce the viscosity, a biocompatible coloring agent to improve visibility during open surgery, an antioxidant to improve shelf life and the like may be added.

The liquids or low melting biodegradable polymers described in this invention may be used for localized drug delivery inside a living body or body cavity. The biodegradable polymer may be melted inside or outside the body using a suitable technique such as heating, laser irradiation, sonication etc. The melted polymer is then transported to the localized site inside the human or animal body or body cavity, preferably using MIS technique. The melted biodegradable polymer is then deposited in an amount that is sufficient for a given application. For example, filling the body cavity generated by tooth extraction and filling a fractured bone defect will require different quantities of the biodegradable polymer. The polymer then conforms to the shape of the body cavity and solidifies. The solidified polymer is thus molded 'in situ' inside the human or animal body cavity.

Biodegradable Coatings and Biodegradable Medical Devices

The biodegradable radio-opaque compositions made in accordance with the present invention find utility in manufacturing of fibers, films, moldings and laminates for medical and surgical applications. These compositions also could be used in medical device fabrication. These devices are prepared by conventional fabrication techniques. In one embodiment, a radio-opaque terminated polymer is mixed or blended with other biodegradable polymers to produce a blend with desirable properties. Solutions of this mixture is then either casted after removing the solvent or by pressing solid copolymers in hydraulic press having heated plates. This results in formation of films that are used for medical and surgical applications. Other methods of manufacturing include melt casting, solvent casting, pressing, compression molding, injection molding, and extrusion. Various techniques such as slow cooling, rapid cooling, quenching may be employed to obtain a desired morphology of processed solids. The radio-opaque polymers produced in according with the present invention can be modified further, by the addition of pharmaceutically acceptable: antioxidant, plasticizer, coloring agent, filler, and the like.

The biodegradable iodinated end-capped polymers of the present invention are also useful in the manufacturing of molded solid surgical aids. Low molecular weight polymers with high iodine content are used as plasticizers for commercial biodegradable polymers. Some of the compositions described herein can be used as scaffolds for tissue engineering applications. Some of the iodinated end-capped polymers produced in accordance with the present invention also find utility in coating biodegradable fibers, filaments or suture materials. It will be apparent to a person skilled in the art that other variations of the present invention may find related applications.

The biodegradable radio-opaque polymers described in this invention may be used to make biodegradable coatings for implantable devises, as material for guided tissue regeneration, for postoperative adhesion prevention, and controlled drug delivery. Examples of biodegradable medical devices include, but are not limited to biodegradable stents that may be used in angioplasty or biodegradable, sutures, screws, staples, biodegradable spinal implants and cages etc. The radio-opaque coating permits easy visualization during a surgical procedure and also confirms the implant's position after surgery. Such coatings may be formed by polymeric coating methods known in the art. For example, in one embodiment, a spray drying or dip coating process may be used in coating a biodegradable medical device. In another embodiment, dip coating may be used to coat a biodegradable stent.

In an embodiment of the invention, the polymer is used to coat Nitinol based medical devices such as coronary or peripheral stents and stent grafts. The coating may be carried out using spry or dip coating method.

In another embodiment of the invention iodinated compositions described in this invention may also be physically mixed or blended to produce a radio-opaque biodegradable device. Radio-opaque compound such as Iohexol is added to polymer mixture in the range of 0.1% to 90%, more precisely in the 5% to 30% range.

Biopsy Markers

In various embodiments of the inventions, surgical biopsy markers are made by combination of hydrophobic and hydrophilic biodegradable polymers. In another embodiment of the invention, water soluble polymers such polyethylene glycol (molecular weight 20000 g/mole) is blended with radio-opaque contrast agents and/or magnetic resonance imaging compounds. In an embodiment of the invention, various mixtures of polyethylene glycol, molecular weight 20000 g/mole (PEG 20K) and sodium diatrizoate dehydrate (SD) were mixed and heated at 70° C. for 30 minutes in a cylindrical mold. The PEG melts and acts a binder for SD particles. The mixture is cooled, isolated and loaded in a 3 ml polypropylene syringe. The syringe was imaged using a standard medical x-ray imaging equipment. The quality of x-ray image is assessed as no image or poor image, acceptable, good, and very good The amount of PEG and SD used and the quality of image obtained is summarized in Table 8.

TABLE 8

| Sodium diatrizoate (g) | PEG 20K (g) | Calculated iodine content of mixture (%) | Quality of X-ray image |
|---|---|---|---|
| 0 | 1.0 | 0 | No image |
| 0.088 | 0.911 | 5 | Acceptable |
| 0.177 | 0.824 | 10 | Good |
| 0.265 | 0.735 | 15 | Good |
| 0.353 | 0.647 | 20 | Very good |
| 0.441 | 0.559 | 25 | Very good |
| 0.530 | 0.471 | 30 | Very good |

In another embodiment, 10 g of polyethylene glycol is mixed with 15 g iohexol (a standard radio-opaque contrast agent). The mixture is heated to 60° C. to melt polyethylene glycol and blended to form a uniform dispersion and cooled. The mixture is filled inside a hollow tube made from biodegradable polymers such as copolymer of polylactones or polyglycolide-polylactate and closed so that the contrast agent mixture is completely covered by the biodegradable polymer. This device can serve as biodegradable surgical marker. Many changes in the size and shape of the device can be made. A spherical or cylindrical device that can be delivered using commercially available surgical biopsy system is preferred. The outer skin of biodegradable polymer on the device prevents the dissolution of the polyethylene glycol and imaging agent filled inside the hollow cavity. After degradation of outer skin, polyethylene glycol and imaging agent iohexol are safely eliminated from the body. In some embodiments, it is preferred to have a synthetic radio-opaque polymer that is radio-opaque and is also porous in nature. The porosity is deliberately created to make the radio-opaque polymer visible in ultrasonic imaging technique. Many methods of porosity preparation known in the art used. These include but not limited to: porosity by lyophilization, porosity by entrapping a pressurized gas such a carbon dioxide gas, porosity induced by salt leaching methods, porosity formed by foam producing compounds such as sodium bicarbonate. In one exemplary embodiment, porosity is created by lyophilizing a solution of radio-opaque polymer. In one exemplary embodiment, a 10% solution of polylactide-co-polyglycolide (50:50) in dioxane in cylindrical mold along with iopamidol (25% by weight) is frozen by cooling at the solution to −20° C. The dioxane solvent is then sublimed around 0° C. under vacuum (lyophilization) to form a porous biodegradable polymer that has at least 10% organically bound iodine. The synthetic biodegradable radio-opaque foam may be useful as surgical biopsy marker especially breast biopsy marker.

Many iodinated compositions described in this invention are susceptible for degradation when exposed to high energy electromagnetic radiation such as ultraviolet light, and gamma radiation. Therefore, sterilization procedures which use ultraviolet light and gamma radiation are least preferred in making medical devices and pharmaceutical compositions. The preferred methods of sterilization for radio-opaque compositions described in this invention include any method which does not us high-energy electromagnetic radiation and include but not limited to: ethylene oxide, propylene oxide, hydrogen peroxide, ozone, and iodine based sterilization methods known in the medical device or pharmaceutical dosage preparation art. Steam or heat based sterilization may also be used. Ethylene oxide based sterilization method is most preferred.

The following non-limiting examples are intended to illustrate the inventive concepts disclosed in this document. Those skilled in the art will appreciate that modifications can be made to these examples, drawings, illustrations and claims, which are intended to fall within the scope, the present invention.

Materials and Equipment

Polyethylene glycol can be purchased form various sources such as Shearwater Polymers, Dow Chemicals (Union Carbide), Fluka and Polysciences. Multifunctional hydroxyl and amine terminated polyethylene glycol are purchased from Shearwater Polymers (Nektor Therapeutics, Huntsville Ala.), Dow Chemicals and Texaco. Amine terminated polyethylene glycols also can be synthesized using methods known in the prior art. Dicyclohexylcarbodiimide (Product Number: D8,000-2), N-(3-Dimethylaminopropyl)-N-ethylcarbodiimide hydrochloride (EDC) (Product Number: 03450) are purchased from Sigma-Aldrich. Pluronic® and Tetronic® series polyols can be purchased from BASF Corporation or Sigma-Aldrich. Cyclic lactones, useful for syntheis of biodegradable polymers, such as DL-lactide, glycolide, caprolactone and trimethylene carbonate can be obtained from commercial sources like Purac, DuPont, Polysciences, Aldrich, Fluka, Medisorb, Wako and Boehringer Ingelheim. N-hydroxysulfosuccinimide can be purchased from Pierce and Sigma-Aldrich. Iodinated compounds like Metrizamide (Product Number: 69753), 3,5-Bis(acetylamino)-2,4,6-triiodobenzoic acid, sodium salt (product Number: 33469) 2,3,5-Triiodobenzyl alcohol (Product Number: 52,690-8) triiodobenzoic acid can be purchased from Sigma-Aldrich. Alternatively, commercially available x-ray contrast media solutions such as ISOVUE™-300 solution can be purchased from local pharmacy. The contrast medial solutions may be lyophilized to recover the iodinated compound. Biodegradable polymers such as polylactide, polyglycolide, polycaprolactone and their derivatives and copolymers can be purchased from Sigma-Aldrich, and Polysciences. All other reagents, solvents are of reagent grade and can be purchased from commercial sources such as Polysciences, Fluka, ICN, Aldrich and Sigma. Most of the reagents/solvents are purified/dried using standard laboratory procedures such as described Perrin et al. Small laboratory equipment and medical supplies can be purchased from Fisher, VWR or Cole-Parmer.

General Analysis

Chemical analysis for the polymers synthesized include structural determination using nuclear magnetic resonance (proton and carbon-13), infrared spectroscopy, high pressure liquid chromatography and gel permeation chromatography (for molecular weight determination). Thermal characterization such as melting point and glass transition temperature can be done by differential scanning calorimetric analysis. The aqueous solution properties such as self assembly, micelle formation, gel formation can be determined by fluorescence spectroscopy, UV-visible spectroscopy and laser light scattering instruments. Mechanical properties such as tensile strength, modulus, percent elongation at break are determined using Instron.

In vitro degradation of the polymers is followed gravimetrically at 37° C., in aqueous buffered medium such as phosphate buffered saline (pH 7.2). In vivo biocompatibility and degradation life times are assessed by injecting or forming a gelling formulation directly into the peritoneal cavity of a rat or rabbit and observing its degradation over a period of 2 days to 12 months. Alternatively, the degradation is assessed by the prefabricated sterile implant made by process like by solution casting. The implant is then surgically implanted within the animal body. The degradation of the implant over time is monitored gravimetrically or by chemical analysis. The biocompatibility of the implant can be assessed by standard histological techniques. Drug elution profiles are measured high pressure liquid chromatography.

EXAMPLE 1

Polymeric Liquid Contrast Agent
Synthesis of Polyethylene Glycol 400 Terminated with Triiodobenzoate A 3 necked flask equipped with magnetic stirrer and nitrogen inlet is charged with 5 g polyethylene glycol, molecular weight 400 and 50 ml DMF. The solution is cooled 0° C. using ice bath and 13.7 g triiodobenzoic acid and 7.5 g 1,3-dicyclohexyl carbodiimide are added to the reaction mixture. The mixture is stirred at 0° C. for 6 h and then overnight at room temperature under nitrogen atmosphere. Dicyclohexylurea is removed by filtration and triiodobenzoate ester is by isolated by removing DMF under vacuum. A toluene solution of crude product is purified by column chromatography using alumina. The final product, a viscous oily liquid is stored in amber colored vial under nitrogen atmosphere at 4° C. The product shows at least 1 g/100 ml solubility in water.

EXAMPLE 2

Synthesis of Triiodophenol Ester of Polyethylene Glycol 600 Diacid 5 g Polyethylene glycol 600 diacid is dissolved in 100 ml dry dichloromethane. The solution is cooled to 4° C. 4.9 g 1,3-dicyclohexyl carbodiimide (DCC) and 8.6 g triiodophenol are added to the reaction mixture. The mixture is stirred at 4° C. for 6 h and overnight at room temperature under nitrogen atmosphere. Dicyclohexylurea is removed by filtration and the PEG ester is by isolated by removing the dichloromethane. It is further purified by column chromatography using alumina as a substrate and toluene as a mobile phase. The product is stored under nitrogen atmosphere at −20° C.

EXAMPLE 3

Synthesis of Polyethylene Glycol Terminated with Triiodophenol by Ethoxylation of Triiodophenol 10 g triiodophenol is charged into flame dried 250 ml reaction flask. The phenol is then heated to 60° C. under vacuum for 24 h to remove traces of moisture from the phenol. 50 ml anhydrous tetrahydrofuran (THF) is added under nitrogen atmosphere. After complete dissolution of the polymer in THF, 3.5 g of potassium naphthalide is added under nitrogen atmosphere. The reaction flask is then cooled to 0° C. using ice-bath and 22 g of ethylene oxide is added using a cold syringe. The reaction is continued at 0° C. for 72 h under nitrogen atmosphere. At the end of 72 h period, 1 ml water is added to the THF solution and the mixture is stirred for another 1 h. It is then added to 4000 ml cold hexane to precipitate the polymer. The polymer is purified by several precipitations from toluene-hexane solvent non-solvent system and dried under vacuum at 60° C. for 24 our. Using a similar procedure, ethylene oxide polymerization may be initiated using hydroxy groups and primary and secondary amine hydrogen atoms on iohexol, Metrizamide, iopamidol, iopentol, iopromide, and Ioversol. The molar ratio of ethylene oxide to initiating group will determine the degree of polymerization of polyethylene glycol chain.

EXAMPLE 4

Synthesis of Three Arm Polyethylene Glycol Terminated with Triiodobenzoate

A 250 ml 3 necked flask equipped with magnetic stirrer and nitrogen inlet is charged with 5 g polyethylene glycol (molecular weight 1000 Daltons, 3 arms, 3 terminal hydroxyl groups per molecule) and 130 ml benzene. 20 ml benzene is distilled out to remove traces of moisture from the solution. The solution is then cooled 4° C. and 12.5 g triiodobenzoic acid and 6.7 g of 1,3-dicyclohexyl carbodiimide are added to the reaction mixture. The mixture is stirred at 4° C. for 6 h and overnight at room temperature under nitrogen atmosphere. Dicyclohexylurea is removed by filtration and triiodo derivative is isolated by removing the benzene under vacuum and repeated precipitation using toluene-hexane solvent-nonsolvent system. The viscous liquid oily product is stored under nitrogen atmosphere at 4° C. until further use.

EXAMPLE 5

Synthesis of Polyethylene Glycol Terminated with Erythrosin

A solution of Erythrosin (acid form, 9.7 g), N,N'-dicyclohexylcarbodiimide (2.93 g), polyethylene glycol (molecular weight 1000 Daltons, 5.0 g) and dimethylaminopyridine (0.148 g) in 100 ml dry DMF is stirred at 0° C. for 16 h under nitrogen atmosphere. The reaction mixture is then filtered to remove urea. The solvent is removed from the filtrate using vacuum distillation to yield a crude product. The crude product is then dissolved in 10 ml toluene and added to 1000 ml ice-cold hexane. The precipitated PEG having terminal Erythrosin group is isolated and dried overnight under vacuum at 60 0° C. UV-VIS spectrum of PEG endcapped product shows absorption in VIS region.

EXAMPLE 6

Synthesis Polyethylene Glycol Triiodobenzoate 5 g polyethylene glycol, molecular weight 1000, is dissolved in 100 ml dry DMF. The solution is cooled to 4° C. and 2.9 g of 1,3-dicyclohexyl carbodiimide (DCC) and 5.5 g triiodobenzoic acid are added to the reaction mixture. The mixture is stirred at 4° C. for 6 h and overnight at room temperature under nitrogen atmosphere. Dicyclohexylurea is removed by filtration and the triiodo derivative is by isolated by removing the DMF under vacuum and repeated precipitation using toluene-hexane solvent-nonsolvent system. The product is stored under nitrogen atmosphere at −20° C.

EXAMPLE 7

Synthesis of Polyethyleneglycol Triiodobenzamde Using Amine Terminated Polyether (Jefffamine®)

10 g Jefffamine® (Jefffamine® ED-2003 or Huntsman XTJ-502, average molecular weight 1900) is dissolved in 200 ml dry DMF. The solution is cooled to 4° C. 2.9 g of 1,3-dicyclohexyl carbodiimide (DCC) and 5.5 g triiodobenzoic acid are added to the reaction mixture. The mixture is stirred at 4° C. for 6 h and overnight at room temperature under nitrogen atmosphere. Dicyclohexylurea is removed by filtration and PEG-triiodobenzamde by isolated by removing the DMF under vacuum and repeated precipitation using toluene-hexane solvent-nonsolvent system. The product is stored under nitrogen atmosphere at −20 C.

EXAMPLE 8

Synthesis of 8 Arm Polyethylene Glycol Terminated with Triiodobenzamde 10 g 8 arm amine terminated polyethylene glycol, molecular weight 20000 (Shearwater, custom synthesized from 8 arm 20000 polyethylene glycol) is dissolved in 200 ml dry toluene. 20 ml toluene is removed by distillation and then the solution is cooled to 4° C. 1.1 g 1,3-dicyclohexyl carbodiimide (DCC) and 2.0 g triiodobenzoic acids are added to the reaction mixture. The mixture is stirred at 4° C. for 6 h and overnight at room temperature under nitrogen atmosphere. Dicyclohexylurea is removed by filtration and PEG-triiodobenzamde by isolated by precipitating in ether. It is then purified by repeated precipitation using toluene-hexane solvent-nonsolvent system. The product is stored under nitrogen atmosphere at −20 C until further use.

EXAMPLE 9

Synthesis of PEO-PPO-PEO Block Copolymer Terminated with Triiodobenzoate

Synthesis of Thermosensitive Radio-Opaque Polymer 20 g PEO-PEO-PEO block copolymer, molecular weight 8000, PEO content >70% (Pluronic F68 obtained from BASF corporation) is dissolved in 200 ml dry toluene. 20 ml toluene is removed by distillation and then the solution is cooled to 4° C. 1.5 g 1,3-dicyclohexyl carbodiimide (DCC) and 2.4 g triiodobenzoic acids are added to the reaction mixture. The mixture is stirred at 4° C. for 6 h and overnight at room temperature under nitrogen atmosphere. Dicyclohexylurea is removed by filtration and PEG-triiodobenzamde by isolated by adding the filtrate in 5000 ml ether. It is then purified by repeated precipitation using toluene-hexane solvent-nonsolvent system A 30% solution of this polymer in saline shows thermoreversible gelation. When the solution is cooled to 4 degree C., it forms a clear liquid. Upon warming to 37 degree C., the solution forms viscous gel. Upon cooling, the gel forms solution again (thermoreversible gelation). The solution as well as gel show better contrast in x-ray imaging when compared to the unmodified polymer. Thus the polymer solution displays better visibility under x-ray imaging as well as thermoreversible gelation property.

The thermoreversible described above gelation may be carried out 'in situ' on the tissue or inside a body cavity during a surgical procedure. A hydrophobic bioactive compound such as paclitaxel may be dissolved in solution or gel and released in a controlled manner.

EXAMPLE 10

Aqueous Compositions for Medical X-Ray Imaging (as a Contrast Agent)

In a 100 ml volumetric flask, 30 ml distilled water, 40 g Jefffamine® triiodobenzamde (Example 7), 0.15 g triethanol amine, 0.19 g triethanol amine hydrochloride, and 0.36 g sodium chloride are added and the mixture is shaken till all components are dissolved. The final volume of the solution is adjusted to 100 ml using distilled deionized water. The solution is filter sterilized using 0.2 micron filter. Alternately, the solution can be steam sterilized.

EXAMPLE 11

Aqueous Compositions Comprising Polymeric and Non-Polymeric Non-Ionic Contrast Agents In a 100 ml volumetric flask, 29 ml triethanol amine buffer (pH 7.2), 28 g PEG 2000 triiodobenzamde (Example 7) and 43 g Iohexol (5-[N-(2,3-Dihydroxypropyl)acetamido]-2,4,6-triiodo-N,N-bis(2,3-dihydroxypropyl)isophthalamide) are mixed. The final volume is adjusted to 100 ml using triethanol amine buffer solution. The solution is filter sterilized.

EXAMPLE 12

Aqueous compositions for X-ray imaging comprising antioxidant, defoaming agent, and viscosity reducing agent In a 100 ml volumetric flask, 30 ml distilled water, 40 g Jefffamine® triiodobenzamde 0.15 g triethanol amine, 0.19 g triethanol amine hydrochloride, 0.36 g sodium chloride and 0.005 g BHT dissolved in 8 ml ethanol are added. The mixture is shaken till all components are dissolved. 0.2 g 1-octanol is added to the mixture and the final volume of the solution is adjusted to 100 ml using distilled deionized water. The solution is filter sterilized using 0.2 micron filter.

EXAMPLE 13

Polymeric Neat Liquids as Contrast Agent 20 g anhydrous ethanol and 80 g PEG 1000 triiodobenzoate are mixed in 250 ml volumetric flask. The solution is warmed to 50° C. for 1 h to form a homogeneous solution. The solution is filtered using 0.2 micron filter and stored until use.

EXAMPLE 14

Contrast Agent Formulation in Water Miscible Organic Solvents 10 g anhydrous ethanol, 10 g n-methyl pyrrolidinone and 80 g PEG 1000 triiodobenzoate are mixed in a 250 ml volumetric flask. The solution is warmed to 50° C. for 1 h to form a homogeneous solution. The solution is filtered using 0.2 micron filter and stored until use.

EXAMPLE 15

Contrast Agent Formulation Where Polymer Shows Self Assembly of Iodine Moieties in Aqueous Solution In a 100 ml volumetric flask, 40 ml triethanol amine buffer (pH 7.2), 25 g PEG 20000 triiodobenzamde with 8 arms (example 8) and are mixed. The final volume is adjusted to 100 ml using triethanol amine buffer solution. The solution is filter sterilized using 200 micron filter.

EXAMPLE 16

Radio-Opaque Biodegradable Crosslinkable Polymer Composition a) Synthesis of Crosslinkable Hydrophobic Synthetic Biodegradable Polymer Part 1: Preparation of trifunctional caprolactone-lactate liquid copolymer Trimethylol propane triol (TMPT) is dried under vacuum at 60° C. for 16 hours. 2 g of dry TMPT, 17.5 g of dl-lactide, and 20 mg of stannous octoate are charged into a 3 necked flask equipped with Teflon coated magnetic stirring needle and nitrogen inlet. The flask is then immersed into silicone oil bath maintained at 160° C. The reaction is carried out for 5 h under nitrogen atmosphere. The reaction mixture is then cooled to room temperature. The mixture is then dissolved in 10 ml toluene. The hydroxy terminated liquid lactate polymer is isolated by pouring the toluene solution in large excess cold hexane. It is further purified by repeated dissolution-precipitation process from toluene-hexane solvent-nonsolvent system and dried under vacuum at 60° C. It is then immediately used for acrylate end capping reaction mentioned below:

Part 2: End Capping of Trifunctional Polylactide Polymer with Acrylate Group 10 g of TMPT initiated lactate synthesized previously is dissolved in 150 ml dry benzene and 2.7 ml of triethyl amine. 20 ml benzene is distilled out. The solution is cooled to 0° C. in ice bath. 1.8 ml acryloyl chloride is added dropwise to the cold lactate solution. The mixture is refluxed under nitrogen atmosphere for 3 h. The solution is filtered to remove triethylamine hydrochloride. The acrylate ester is then isolated by pouring the filtered solution in large excess cold hexane. It is further purified by repeated (3 times) precipitation from toluene-cold hexane system. The liquid polymer is dried under vacuum at 40° C. It is stored in amber colored bottle under nitrogen atmosphere.

b) Radio-Opaque Crosslinkable Biodegradable Polymer

The liquid crosslinkable polymer is made radio-opaque by dispersing/dissolving commercially available contrast agents such as Iohexol prior to crosslinking. Thus, 2 grams of polymer is mixed with 1 g of iohexol and 0.010 g benzoyl peroxide. The mixture is heated to 60 degree C. until gelation and crosslinking. The crosslinked polymer undergoes degradation upon implantation while Iohexol in the polymer provides visibility in x-ray imaging. Iohexol may be added in 0.1% to 89% weight range. The preferred range is between 5 to 30%. The liquid acrylate polymer can be free radically polymerized 'in situ' inside the human body. The preferred way is visible light initiated photopolymerization. The crosslinking may be performed outside prior to implantation. The radio-opaque polymer may be of used to make radio-opaque microspheres.

EXAMPLE 17

Synthesis of Low Temperature Melting (<60° C.) Radio-Opaque Injectable Polymeric Composition 2.00 g polyethylene glycol 2000, 7.2 g of dl-lactide, 5.7 g caprolactone and 30 mg of stannous octoate are charged into 100 ml Pyrex pressure sealing tube. The tube is frozen in liquid nitrogen and connected to vacuum line for 10 minutes. The tube is then connected to argon gas line and sealed under argon. The sealed tube is immersed in oil bath maintained at 140° C. The polymerization is carried out for 16 h at 140° C. The polymer from the tube is recovered by breaking the Pyrex tube. The polymer is then dissolved in 20 ml chloroform and precipitated in 2000 ml hexane. The precipitated polymer is recovered by filtration and dried under vacuum for 1 day at 60° C.

The injectable polymer synthesized above is mixed with iodinated compounds such as Iohexol prior to injecting into human body. The Iohexol biodegradable polymer mixture is melted "in situ" at al localized site inside the body during a surgical procedure. The presence of Iohexol makes the polymer radio-opaque. The amount of iohexol in the polymer may range from 5% to 60%. The iodine content of final composition may range from 5 to 30% more preferably 10-20%.

EXAMPLE 18

Coating of Biodegradable Stent Using Biodegradable Coating Comprising Iodinated Compounds or Biodegradable Radio-Opaque Ink.

1 g Polylactide-co-polyglycolide (50:50) copolymer (average molecular weight 25000-50000) is dissolved in 100 ml dimethyl sulfoxide. To this solution 400 mg Iohexol (exemplary water soluble, non-ionic radio-opaque compound) is added. The solution/suspension is used in coating various biodegradable polymeric devices. The solution could also be used as a biodegradable radio-opaque ink. The coating solution may be added with bioactive compounds such as Paclitaxel or Rapamycin to reduce restenosis.

Coating of Biodegradable Stents Using Biodegradable Radio-Opaque Coating Composition A balloon expandable biodegradable stent fabricated using synthetic biodegradable polymers such as polyhydroxy acids or polylactones is expanded and dip coated or spray coated using coating solution mentioned above. The coated stent is dried in air and finally in vacuum at 60° C. for 24 h. The coated stent is compressed and mounted on angioplasty balloon and stent catheter delivery system. The stent and its delivery system is sterilized using ethylene oxide. The stent is then deployed using balloon angioplasty technique and expanded in situ at the site of blockage. The biodegradable stent is visible during deployment due to biodegradable radio-opaque coating. Alternatively suspension of silver salts such as silver chloride, silver acetate, and silver lactate may be used in place of iodinated compound. The coating thickness on stent may range from 2 micron to 2000 microns, more preferably 10 to 50 microns. The iodine content of coating may range from 5 to 40%, preferably 10 to 30% to provide sufficient visibility of stent during deployment.

EXAMPLE 19

X-Ray Visible Injectable Controlled Release Drug Composition 2.00 g polyethylene glycol 2000, 7.2 g of dl-lactide, 5.7 g caprolactone and 30 mg of stannous octoate are charged into 100 ml Pyrex pressure sealing tube. The tube is frozen in liquid nitrogen and connected to vacuum line for 10 minutes. The tube is then connected to argon gas line and sealed under argon. The sealed tube is immersed in oil bath maintained at 140° C. The polymerization is carried out for 16 h at 140° C. The polymer from the tube is recovered by breaking the Pyrex tube. The polymer is then dissolved in 20 ml chloroform and precipitated in 2000 ml hexane. The precipitated polymer is recovered by filtration and dried under vacuum for 1 day at 60° C.

3.5 g of polymer synthesized as above is mixed with 0.5 g of rifampin, 1.5 g of Iopamidol and 25 ml tetrahydrofuran and 25 ml dimethyl sulfoxide. The mixture is warmed to 40 to prepare a homogeneous mixture. It is filtered through 0.2 micron filter. The solvents are removed under vacuum. The polymer mixture is sterilized by ethylene oxide and injected into a dental cavity created by removal of tooth. The polymer mixture is visible when viewed using medical x-ray imaging techniques. A rifampin release from the mixture demonstrates a release of bioactive compound.

EXAMPLE 20

In situ Melting of Injectable Formulation Comprising Iodinated Compound 3 g Polycaprolactone (molecular weight 2000) and 0.25 g rifampin and 1.0 g 3,5-Bis(acetylamino)-2,4,6-triiodobenzoic acid are dissolved/suspended in 10 ml dimethyl sulfoxide. Solvent is removed air drying in chemical hood and finally under vacuum at 60° C. for 24 hours. The mixture is filled in a special syringe which can be heated to 60° C. and is sterilized using ethylene oxide. The polymer composition is heated to 55° C. and melted. The melting is done just prior to implantation or in situ in side the body. This melted mixture is used in the surgical procedure where it is used to fill a body cavity.

EXAMPLE 21

Solvent Based Radio-Opaque Biodegradable Injectable Composition

Biodegradable Polymer and Iodinated Organic Compound Dissolved in Water Miscible Organic Solvent and Injected in situ During a Surgical Procedure 1 g Polylactide, molecular weight 2000 (PLA), 0.2 g Iohexol are dissolved/dispersed in 10 ml n-methyl pyrolidonone (NMP). The mixture is transferred into a 20 ml sterile syringe. The mixture is used in coating an organ or filling a tissue cavity. The NMP is miscible with tissue fluids and washes away leaving behind a PLA and Iohexol. The implanted PLA with Iohexol can be viewed using medical x-ray imaging techniques. In place of Iohexol, other radio-opaque agents such as Metrizamide, iopamidol, iopentol, iopromide, and Ioversol may also be used. Silver salts may also be used to make the biodegradable polymer radio-opaque. The percentage of radio-opaque compound such as Iohexol in the polymer may be varied; it may be ranged between 0.1% to 90%, more preferably from 5% to 40%.

EXAMPLE 22

Synthesis of Rose Bengal Terminated Polyethylene Glycol 2 g of PEG 1000 (molecular weight 1000 Daltons) is dissolved in 100 ml dry benzene. About 50 ml of benzene is distilled out to remove traces of water from the PEG solution. The warm solution is cooled to room temperature and, 50 ml dry acetone and 4.068 g of Rose Bengal (free acid form) and 1 drop of sulfuric acid are added. The reaction mixture is refluxed for 4 h. The solution is then cooled and filtered. The filtrate is added to 2000 ml cold hexane. The precipitated Rose Bengal terminated polymer is dried at 60° C. under vacuum for 24 h.

EXAMPLE 23

Visibility of PEG End Capped with Iodine Containing Compounds Using Medical X-Ray Imaging Technique 1 ml of neat liquid polymer with triiodobenzoate group synthesized according to earlier example is placed into 1 ml graduated pipette. The tube is sealed on both sides using adhesive tape. This glass pipette is glued onto a sheet of paper and a 15 mm thick Plexi glass sheet is kept on top of tube (to simulate the x-ray absorption by the human chest) and X-ray photographs of the pipette are taken using a fluoroscope (made by Siemens). The x-ray absorption due to PEG triiodo liquid ester is clearly seen in the developed x-ray film.

EXAMPLE 24

Coating of Biodegradable Devices Using Biodegradable Coating Comprising Iodinated Compounds. Coating Using Blends of Two Biodegradable Polymers 3 g Polylactide-co-polyglycolide (50:50) copolymer (average molecular weight 25000-50000) is dissolved in 100 ml chloroform. To this solution 0.1 g polylactic acid or polycaprolactone, molecular weight 1000, endcapped with triiodobenzoic acid is added (see examples 25 for synthesis). The solution is used in coating various biodegradable polymeric devices.

Coating of Vicryl Suture:

The Iohexol solution prepared above is loaded into standard spry painting apparatus. The solution is spray coated on 4-0 Vicryl sutures (Ethicon Inc). The coated sutures are dried on vacuum at 60° C. for 24 h. The coated suture is sterilized using ethylene oxide. The coated sterile suture is used in joining soft tissue in an animal surgery. The coated suture is visible when viewed using standard medical x-ray apparatus. The suture may also be dip coated. If needed, iodinated compounds such as Iohexol may be added in coating formulation to increase iodine content and therefore image quality of the coating.

EXAMPLE 25

Preparation of Oligo Polylactic Acid End-Capped with Two Iodinated End Groups

Part 1: Synthesis of Polylactic Acid 2.00 g of diethylene glycol, 16.28 g of dl-lactide and 30 mg of stannous octoate are charged into 100 ml Pyrex pressure sealing tube. The tube is frozen in liquid nitrogen and connected to vacuum line for 10 minutes. The tube is then connected to argon gas line and sealed under argon. The tube is then immersed in oil bath maintained at 140° C. The polymerization is carried out for 16 h at 140° C. The polymer from the tube is recovered by breaking the Pyrex tube. The polymer is then dissolved in 30 ml chloroform and precipitated in cold 2000 ml hexane. The precipitated polymer is recovered by filtration and dried under vacuum for 1 day at 60° C. It then immediately used in end-capping reaction.

Part 2: End-Capping of Polylactic Acid with Triiodobenzoyl Chloride 5 g of PLA (synthesized previously) is dissolved in 150 ml dry toluene. About 50 ml of toluene is distilled to remove traces of water from the reaction mixture. The warm solution is cooled to 30° C. To this warm solution, 1.3 ml of triethyl amine and 5.9 g of triiodobenzoyl chloride are added. The reaction mixture is then refluxed for 2 h and filtered. The product is precipitated by adding the filtrate to 2000 ml cold dry hexane and filtration. It is then dried under vacuum for 12 h at 50° C.

EXAMPLE 26

Preparation of 5 Arm Polycaprolactone Terminated with Triiodobenzoic Acid

Part 1: Preparation of Xylitol Initiated Polycaprolactone 2 g of xylitol, 22.5 g of caprolactone and 30 mg of stannous octoate are charged in a 100 ml glass sealing tube. The tube is then sealed under argon atmosphere. The sealed tube is then heated in silicone oil bath maintained at 160° C. The contents of the tube are manually shaken for every 10 minutes. The reaction continued for 18 hours. At the end of the reaction, the tube is cooled to room temperature and the xylitol caprolactone is isolated by breaking the glass tube. The polymer is further purified by precipitation from toluene-hexane solvent-nonsolvent system. It is dried overnight under vacuum at 60° C.

Part 2a: End Capping of Xylitol Polycaprolactone with Triiodobenzoic Acid 10 g of xylitol caprolactone is dissolved in 300 ml dry toluene. About 30 ml of toluene is distilled off from the solution to remove the traces of moisture absorbed during the previous synthesis workup. The mixture is cooled to 0-30° C.

and 14.8 g triiodobenzoic acid and 7.9 g 1,3-dicyclohexyl carbodiimide are added to the reaction mixture. The mixture is stirred at 4° C. for 6 h and overnight at room temperature under nitrogen atmosphere. Dicyclohexylurea is removed by filtration and triiodo derivative is isolated by removing the benzene under vacuum and repeated precipitation using toluene-hexane solvent-nonsolvent system. The viscous liquid oily product is stored under nitrogen atmosphere, in amber color vial, at 4 C until further use.

Part 2b: End Capping of Xylitol Polycaprolactone with 3,5-Bis(acetylamino)-2,4,6-triiodobenzoic Acid 10 g of xylitol caprolactone is dissolved in 300 ml dry dimethylfroamamide. About 30 ml of toluene is distilled off from the solution to remove the traces of moisture absorbed during the previous synthesis workup. The mixture is cooled to 0-30° C. and 19.2 g 3,5-Bis(acetylamino)-2,4,6-triiodobenzoic acid and 7.9 g 1,3-dicyclohexyl carbodiimide are added to the reaction mixture. The mixture is stirred at 4° C. for 6 h and overnight at room temperature under nitrogen atmosphere. Dicyclohexylurea is removed by filtration and triiodo derivative is isolated by removing the dimethylformamdie under vacuum and repeated precipitation using toluene-hexane solvent-nonsolvent system. The viscous liquid oily product is stored under nitrogen atmosphere, in amber color vial, at 4 C until further use.

EXAMPLE 27

Oligomeric Polyhydroxy Polymer Terminated with Erythrosin

Part 1: Preparation of Trifunctional Lactate Liquid Copolymer

Trimethylol propane triol (TMPT) is dried at 60° C. overnight under vacuum prior to use. 2 g of dry TMPT, 17.5 g of dl-lactide, and 20 mg of stannous octoate are charged into a 3 necked flask equipped with Teflon coated magnetic stirring needle and nitrogen inlet. The flask is then immersed into silicone oil bath maintained at 160° C. The reaction is carried out for 5 h under nitrogen atmosphere. The reaction mixture is then cooled to room temperature. The mixture is then dissolved in 100 ml toluene. The hydroxy terminated liquid lactate polymer is isolated by pouring the toluene solution in large excess cold hexane. It is further purified by repeated dissolution-precipitation process from toluene-hexane solvent-nonsolvent system and dried under vacuum at 60° C. It is then immediately used for end-capping reaction mentioned below:

Part 2a: End Capping of Trifunctional Polymer with Erythrosin 5 g of TMPT initiated lactate is dissolved in 100 ml dry benzene and 9.1 g Erythrosin. The solution is cooled to 0° C. in ice bath. 5.2 g of DCC is added to the cold lactate solution. The mixture is stirred under nitrogen atmosphere for 3 days. The solution is filtered to remove urea and the ester is then isolated by pouring the filtered solution in large excess cold hexane. It is further purified by repeated (3 times) precipitation from toluene-cold hexane system. The polymer is dried under vacuum at 40° C. It is stored in amber colored bottle under nitrogen atmosphere at ° C.

Part 2b: End Capping of Trifunctional Polymer with 3,5-Bis(acetylamino)-2,4,6-triiodobenzoic Acid 5 g of TMPT initiated lactate is dissolved in 100 ml dry benzene and 6.8 g 3,5-Bis(acetylamino)-2,4,6-triiodobenzoic acid. The solution is cooled to 0° C. in ice bath. 5.2 g of DCC is added to the cold lactate solution. The mixture is stirred under nitrogen atmosphere for 3 days. The solution is filtered to remove urea and the ester is then isolated by pouring the filtered solution in large excess cold hexane. It is further purified by repeated (3 times) precipitation from toluene-cold hexane system. The polymer is dried under vacuum at 40° C. It is stored in amber colored bottle under nitrogen atmosphere at ° C.

EXAMPLE 28

Preparation of Blend of Synthetic Biodegradable Polymer and Polyhydroxy Polymers with Iodinated Terminal Groups 1 g polylactide-co-polylactide copolymer (50:50), 1 g iodinated group terminated polylactic acid synthesized previously and 100 ml tetrahydrofuran are dissolved in 500 ml beaker. 80 ml solvent is distilled under vacuum and the concentrated polymer solution is precipitated in 2000 ml cold hexane. The precipitated blend is recovered and dried in vacuum at 30° C. for 24 until constant weight and stored at ° C. under nitrogen atmosphere until further use. The blend can be used in fabrication of various biodegradable medical devices.

EXAMPLE 29 a) Polycaprolactone Diol Terminated with Triiodobenzene 10 g polycaprolactone diol (average molecular weight 1250 purchased from Sigma-Aldrich, USA) is dissolved in 200 ml dry toluene. About 30 ml of toluene is distilled off from the solution to remove the traces of moisture absorbed during the previous synthesis workup. The mixture is cooled to 0° C. and 8.8 g triiodobenzoic acid and 4.7 g 1,3-dicyclohexyl carbodiimide are added to the reaction mixture. The mixture is stirred at 4° C. for 6 h and overnight at room temperature under nitrogen atmosphere. Dicyclohexylurea is removed by filtration and triiodo derivative is isolated by removing the benzene under vacuum and repeated precipitation using toluene-hexane solvent-nonsolvent system. The viscous liquid oily product, is stored under nitrogen atmosphere, in amber color vial, at 4 C until further use.

b) Polycaprolactone Diol Terminated with 3,5-Bis(acetylamino)-2,4,6-triiodobenzoic Acid 10 g polycaprolactone diol (average molecular weight 1250, purchased from Sigma-Aldrich) is dissolved in 200 ml dry dimethylforamide. About 30 ml of dimethylforamide is distilled off from the solution to remove the traces of moisture absorbed during the previous synthesis workup. The mixture is cooled to 0° C. and 11.4 g 3,5-Bis(acetylamino)-2,4,6-triiodobenzoic acid and 4.7 g 1,3-dicyclohexyl carbodiimide are added to the reaction mixture. The mixture is stirred at 4° C. for 6 h and overnight at room temperature under nitrogen atmosphere. Dicyclohexylurea is removed by filtration and triiodo derivative is isolated by removing the benzene under vacuum and repeated precipitation using toluene-hexane solvent-nonsolvent system. The viscous liquid oily product, is stored under nitrogen atmosphere, in amber color vial, at 4° C. until further use.

EXAMPLE 30

Synthesis of Polylactide with Triiodobenzoic Acid as End-Group

Polymerization of Caprolactone and Glycolide Initiated by an Iodinated Compound.

Triiodobenzyl alcohol is dried at 60° C. overnight under vacuum prior to use. 1 g dry Triiodonenzyl alcohol 1.4 g glycolide and 1.5 g caprolactone, and 20 mg of stannous octoate are charged into a 3 necked flask equipped with Teflon coated magnetic stirring needle and nitrogen inlet. The flask is then immersed into silicone oil bath maintained at 160° C. The reaction is carried out for 5 h under nitrogen atmosphere. The reaction mixture is then cooled to room temperature. The mixture is then dissolved in 100 ml toluene. The iodine terminated glycolate-caprolactone polymer is isolated by pouring the toluene solution in large excess cold hexane. It is further purified by repeated dissolution-precipitation process from toluene-hexane solvent-nonsolvent system and dried under vacuum at 60° C. Using a similar procedure other hydroxy containing compounds such as Iohexol can also be used to initiate polymerization of lactones or cyclic carbonates.

EXAMPLE 31

Preparation of Polyethylene Glycol-Polyhydroxy Copolymer Terminated with Radio-Opaque End-Groups
Part 1: Synthesis of Polyethylene Glycol-co-Polyglycolate Copolymer (PEG2KG):
20 grams monomethoxy polyethylene glycol, molecular weight 2000 (PEG2K) is dried at 100° C. for 16 hours prior to use. 20 grams PEGM2K, 5.8 g of glycolide and 25 mg of stannous 2-ethylhexanoate are charged into a 3 necked flask equipped with a Teflon coated magnetic stirring needle. The flask is then immersed into silicone oil bath maintained at 160° C. The polymerization reaction is carried out for 16 h under nitrogen atmosphere. At the end of the reaction, the reaction mixture is dissolved in 100 ml toluene. The hydroxy terminated glycolate copolymer is isolated by pouring the toluene solution in 4000 ml cold hexane. It is further purified by repeated dissolution-precipitation process from toluene-hexane solvent-nonsolvent system and dried under vacuum at ° C. It is then immediately used for end capping reaction mentioned below:
Part 2: Esterification of Hydroxyl Groups with Triiodobenzoic Acid.
To a solution of 30 g of PEG2KG in 300 ml dry methylene chloride, 3.5 g triiodobenzoic acid and 1.9 g DCC are added. The reaction mixture is stirred overnight under nitrogen atmosphere. Dicyclohexylurea is removed by filtration. The filtrate is evaporated and the residue obtained is redissolved in 100 ml toluene. The toluene solution is precipitated in 2000 ml hexane. The triiodoester terminated polymer is stored under nitrogen atmosphere until further use.

EXAMPLE 32

Drug Delivery Composition Comprising Non-Polymeric Liquid, an X-Ray Contrast Agent and Bioactive Compound
5 g sucrose acetate (a non-polymeric controlled release medium) and 0.25 g rifampin (bioactive compound) and 0.5 g Iohexol (x-ray absorbing compound) are dissolved/dispersed in 10 m chloroform. Most of the solvent is removed by air drying in chemical hood. Rest of the solvent is removed under vacuum at 60° C. for 24 hours. The mixture is filled in a 20 ml sterile syringe and the entire unit is sterilized by ethylene oxide. This mixture is used in the surgical procedure where it is used to fill a body cavity. Rifampin is released at the site of injection. The Iohexol trapped inside the sucrose acetate improved contrast when viewed using medical x-ray imaging systems. In place of Iohexol, other radio-opaque agents such as Metrizamide, iopamidol, iopentol, iopromide, and Ioversol may also be used. The percentage of radio-opaque compound such as Iohexol in the biocompatible liquid carrier may be varied, it may be ranged between 0.1% to 90%, more preferably from 5% to 30%.

EXAMPLE 33

Synthesis of Water Soluble Activated Triiodobenzoic Acid
Synthesis of n-Hydroxysulfosuccinimide (SNHS) Derivative of Triiodobenzoic Acid
A 3 necked flask equipped with magnetic stirrer and nitrogen inlet is charged with 5 g of triiodobenzoic acid and 20 ml DMF. The solution is cooled 4° C. and 2.4 g of N-hydroxysulfosuccinimide and 2.9 g of 1,3-dicyclohexyl carbodiimide are added to the reaction mixture. The mixture is stirred at 4° C. for 6 h and overnight at room temperature under nitrogen atmosphere. Dicyclohexylurea is removed by filtration and SNHS derivative is by isolated by removing the DMF under vacuum. The compound was further purified by column chromatography

EXAMPLE 34 a) N-Hydroxysuccinimide Ester of Triiodobenzoic Acid or 3,5-Bis(acetylamino)-2,4,6-triiodobenzoic Acid
1.2 g n-hydroxy succinimide and 1.1 g of triethyl amine are dissolved in 100 ml benzene. The solution is cooled to 0° C. in ice bath. 1.2 g triiodobenzoyl chloride is added dropwise to the cold alcohol solution. The mixture is then refluxed under nitrogen atmosphere for 3 h. The solution is filtered to remove triethylamine hydrochloride. The ester is then isolated by removing the solvent. It is further by column chromatography. Using a similar procedure, NHS ester of 3,5-Bis(acetylamino)-2,4,6-triiodobenzoic acid can be synthesized from 3,5-Bis(acetylamino)-2,4,6-triiodobenzoyl chloride
b) N-Hydroxysuccinimide Ester of 3,5-Bis(acetylamino)-2,4,6-triiodobenzoic Acid
A 3 necked flask equipped with magnetic stirrer and nitrogen inlet is charged with 5 g 3,5-Bis(acetylamino)-2,4,6-triiodobenzoic acid and 50 ml DMF. The solution is cooled 4° C. and 0.12 g of N-hydroxysulfosuccinimide and 2.0 g of 1,3-dicyclohexyl carbodiimide are added to the reaction mixture. The mixture is stirred at 4° C. for 6 h and overnight at room temperature under nitrogen atmosphere. Dicyclohexylurea is removed by filtration and n-hydroxysulfosuccimide derivative is isolated by removing the DMF under vacuum. The compound is further purified by column chromatography.

EXAMPLE 35

Synthesis of N-Hydroxysulfosuccinimide Derivative of Erythrosin
A 3 necked flask equipped with magnetic stirrer and nitrogen inlet is charged with 5 g Erythrosin B, acid form and 50 ml DMF. The solution is cooled 4° C. and 0.71 g of N-hydroxysuccinimide and 1.67 g of 1,3-dicyclohexyl carbodiimide are added to the reaction mixture. The mixture is stirred at 4° C. for 6 h and overnight at room temperature under nitrogen atmosphere. Dicyclohexylurea is removed by filtration and n-hydroxysuccimide derivative is isolated by removing the DMF under vacuum. The compound is further purified by column chromatography

EXAMPLE 36

Evaluation of PEG 8-Arm Polymer Terminated with Triiodobenzamde for Blood Pool Imaging
30% solution of PEG 20000, 8-arm polymer terminated with triiodobenzamde in PBS is used in the blood pooling application. This solution is injected into white New Zealand rabbits at a dose of 3 ml/kg as a slow bolus injection. At 0.25 h, 0.5 h, 1 h and 2 h post-injection time interval, the opacification of the spleen liver, and blood pool as measured in the aorta and within the left ventricle is determined by computed tomography (CT) using a Toshiba 900S Imager CT scanner and associated software. The imaging analysis is expected to show that the PEG 8-arm polymer terminated with triiodobenzamde has excellent blood pool, liver and spleen opacification properties. Imaging at 72 hours post injection is expected to should show complete clearance from the blood with partial clearance from the liver and spleen.

EXAMPLE 37

Proteins Chemically Modified Using Triiodobenzoic Acid Derivatives
Human Monoclonal Antibody Modified Using Hydroxysuccimide Ester of Triiodobenzoic Acid.

100 mg of human monoclonal antibody was dissolved in 2 ml sodium borate buffer pH 9. To this solution, 100 mg triiodobenzoic acid n-hydroxysuccimide ester, dissolved in 0.5 ml dimethyl sulfoxide is added (example 34). The reaction mixture is shaken for 10 minutes and the reaction is continued for 12 hours at room temperature. The reaction mixture is then dialyzed with1000 ml distilled water using 10000 molecular weight cutoff dialysis membrane. The reaction mixture is freeze dried to recover the modified antibody. The triiodobenzoic acid substituted antibody is used as a tissue specific x-ray contrast medium.

Using a similar procedure, amine groups of albumin or collagen can be modified with iodinated compounds such as erythrosin or triiodobenzoic acid. The percent of amine group modification will depend on the reaction conditions employed. Amine groups up to 5 to 99% in the collagen could be substituted. Radio-opaque albumin, collagen or antibodies can be useful in many other medical applications.

EXAMPLE 38

Radio-Opaque Implantable Collagen or Animal Tissue
Tissue Modification Using Iodinated Compound
a) Synthesis of N-Hydroxysuccinimide Ester of Triiodobenzoic Acid (TIBA-NHS)

1.2 g n-hydroxy succinimide and 1.1 g of triethyl amine are dissolved in 100 ml benzene. The solution is cooled to 0° C. in ice bath. 1.2 g triiodobenzoyl chloride is added dropwise to the cold alcohol solution. The mixture is then refluxed under nitrogen atmosphere for 3 h. The solution is filtered to remove triethylamine hydrochloride. The ester is then isolated by removing the solvent. It is further by column chromatography.

b) Chemical Bonding of Triiodobenzoic Acid Derivative to the Tissue
Modification Bovine Pericardium Tissue Ten 1 cm by 1 cm bovine pericardium pieces, cut from a freshly obtained bovine pericardial sac, are transferred to 50 ml conical flask containing 10 ml phosphate buffered saline (PBS, (pH 7.2). 250 mg triiodobenzoic acid succinimide ester, TIBA-NHS ester dissolved in 0.5 ml dimethyl sulfoxide is added to the tube and the solution is vortexed for 15 minutes. 0. 1 g of TIBA-NHS in 0.1 ml DMSO is added to the fixation solution every 2 hours upto six hours. The modification reaction is carried for 6 hours at ambient temperature (25° C.) and then for 12 hours at 4° C. with gentle shaking. The reaction is terminated by washing the tissue with 20 ml PBS 3 times. Finally, the tissue is stored in 30 ml 38% isopropanol and 2% benzyl alcohol solution at 4° C. until further use. The triiodobenzoic acid moieties incorporated in the tissue makes the tissue radio-opaque when viewed using medical x-ray imaging techniques.

In another approach, ten 1 cm by 1 cm bovine pericardium pieces, cut from a freshly obtained bovine pericardial sac, are transferred to 50 ml conical flask containing 10 ml MES buffer,(pH 6.5), 2 g 3,5-bis(acetylamino)-2,4,6-triiodobenzoic acid, 2 g Iopamidol, 2 g EDC and 1.5 g n-hydroxysuccinimide are added to the MES solution. After complete dissolution, the tube is transferred to refrigerator and the reaction is continued for 48 hours with occasional shaking. The tissue is removed from the tube and washed with 10 ml PBS 3 times to remove unreacted chemicals. The visibility of iodinated tissue is compared with unmodified tissue using standard medical x-ray equipment. The miffed tissue showed better visibility presumably due to chemically bound iodinated moieties.

EXAMPLE 39

Hydrogel Based Ultrasonic Contrast Agent and Methods for Making the Same.
Part 1: Synthesis of Polyethylene Glycol Lactate Copolymer (PEG20KL5)

50 g PEG molecular weight 20000 is dried at 120° C. under vacuum for 10 hours. 10.0 g dry PEG molecular weight 20000, 2.2 g of dl-lactide and 100 mg of stannous octoate are charged into 100 ml flame dried round bottom flask. The flask is then connected to argon gas line and then immersed in oil bath maintained at 160° C. The polymerization reaction is carried out for 16 h at 160° C. The polymer is then dissolved in 100 ml toluene and precipitated in 2000 ml cold hexane. The precipitated polymer is recovered by filtration and dried under vacuum for 1 day at 60° C. It then immediately used in next step Part 2: End-Capping of PEG20KL5 with Polymerizable or Crosslinkable Group (PEG20KL5A)

30 g of PEG20KL5 is dissolved in 450 ml dry toluene. About 50 ml of toluene is distilled out to remove traces of water from the reaction mixture. The solution is cooled to 65° C. To this warm solution, 0.6 g of triethyl amine and 0.5 g acryloyl chloride are added. The reaction mixture is then stirred for 30 minutes at 50-60° C. and filtered. The reactive crosslinkable precursor is precipitated by adding the filtrate to 2000 ml cold hexane. The precipitated polymer is recovered by filtration. It is then dried under vacuum for 12 h at 50° C.

Part 3: Polymerization of PEG20KL5 to Prepare Microspheres 5 g of PEG20KL5is dissolved in 10 ml PBS. 300 mg Irgacure 652 (2,2-dimethoxy2-phenylacetophenone) is dissolved in 0.7 g n-vinyl pyrrolidinone to prepare a initiator solution. 75 microliter of initiator solution is added to the PEG20KL5 solution and the solution is mixed. The mixture is then poured into 100 mineral oil(high viscosity grade) and stirred vigorously. While stirring, the droplets of PEG20KL5 solution are exposed to long UV ultraviolet light (Black -Ray UV lamp, 360 nm light, 10000 mW/cm2 intensity. The droplets are polymerized into hydrogel microsphere. The viscosity of mineral oil is reduced by adding 20 ml hexane to the mixture and the mixture is filtered to remove polymerized hydrogel particles. The polymerized hydrogel particles are further washed with pure hexane to remove traces of oil from the surface of the particles.

Part 4: Storage of Hydrogel Particles Under Pressurized Carbon Dioxide.

2 g of the hydrogel particles prepared as described in part 3 are stored in thick wall glass vial and the vial is filled with carbon dioxide gas (pressure 0.1 psi to 20 psi. The carbon dioxide dissolves under pressure in the PBS solution inside the hydrogel.

Part 5: Use of Hydrogel Microspheres Stored Under Pressurized Carbon Dioxide Atmosphere as Ultrasonic Contrast Agent The hydrogel containing vial is depressurized just prior to be used as ultrasonic contrast agent. The hydrogel microspheres are dispersed in the 5 ml PBS solution and injected in the human or animal body. The hydrogel particles are visible when viewed using high resolution medical ultrasonic imaging equipment. The carbon dioxide gas dissolved in free water of hydrogel slowly diffuses out of hydrogel surface due to change in pressure. This results into contrast enhancement due to change in density of the hydrogel.

Many types of hydrogel microspheres could be used. Biodegradable hydrogel microspheres made from albumin, polyethylene glycol derivatives are most preferred.

EXAMPLE 40

Radio-Opaque Natural Polymer Based Compositions
Preparation of Radio-Opaque Albumin made Using Zero Length Catalyst In a 50 ml polypropylene centrifuge tube, 1 g of bovine serum albumin and 2 ml commercially available Isovue-300 x-ray contrast agent solution (Iopamidol solution with 30% organically bound iodine) was added. The mixture was stored at 4° C. until albumin is completely dissolved in the solution. To this solution, 0.6 g n-hydroxysuccinimide (NHS) and 1 g 1-ethyl-3-(3-dimethylaminopropyl carbodiimide)hydrochloride (EDC) were added. The reaction was continued at 4° C. for 72 until the liquid is transformed in to gel. The crosslinked hydrogel was washed with 10 ml PBS buffer solution 2 times to remove unreacted EDC, n-hydroxysuccinimide and iodinated compound. A portion of the gel was subjected to x-ray imaging was found to be visible in developed x-ray film.

EXAMPLE 41

Preparation of Radio-Opaque Chitosan
In a 50 ml round bottom flasks, 0.5 g of chitosan is dissolved 10 ml in 0.1M acetic acid solution. To this solution, 3 g 3,5-bis(acetylamino)-2,4,6-triiodobenzoic acid, 2 g EDC and 1 g NHS are added. The reaction is continued at ambient temperature for 6 h and then transferred to refrigerator for 72 h. The solution is then poured in 500 ml acetone to separate chitosan. The precipitated polymer is washed and dried under vacuum and imaged using medical x-ray equipment.

EXAMPLE 42

Preparation of Radio-Opaque Hyaluronic Acid
a) Modification Using 3,5-bis(acetylamino)-2,4,6-triiodobenzoic Acid (Esterification with Hydroxy Groups in Hyaluronic Acid)

In a 500 ml conical flask, 2 g of sodium hyaluronate is dissolved in 100 ml 20 mM MES buffer (pH 6.5). To this solution, 0.5 g NHS and 2 g 3,5-bis(acetylamino)-2,4,6-triiodobenzoic acid are added. After complete dissolution, 2 g EDC is added. The reaction mixture is transferred to refrigerator (4° C.) for 48 h. The solution is then poured in 2 L acetone with constant stirring to isolate modified hyaluronic acid. The precipitated polymer is separated by filtration and redissolved in 100 ml water.

b) Modification of Hyaluronic Acid Using Iopamidol (Esterification of Acid Group in Hyaluronic Acid)

In a 500 ml conical flask, 1 g sodium hyaluronate and 40 ml commercially available Isovue-300 x-ray contrast agent solution (Iopamidol solution with 30% organically bound iodine) are added. After complete dissolution of sodium hyaluronate, 0.6 g n-hydroxysuccinimide (NHS) and 1 g 1-ethyl-3-(3-dimethylaminopropyl carbodiimide) hydrochloride (EDC) are added. The reaction is continued at 4° C. for 48 until. The modified hyaluronic acid derivative is isolated by precipitating it in large excess of acetone and dried in vacuum oven at ambient temperature.

EXAMPLE 43

Preparation of Thermosensitive Radio-Opaque Solution
In a 50 ml polypropylene centrifuge tube, 3.5 g of Pluronic F127, 5 g commercially available Isovue-300 x-ray contrast agent solution (Iopamidol solution with 30% organically bound iodine) and 1.5 g distilled water are added. The mixture is stored at 4° C. until Pluronic is completely dissolved in the solution. The solution is fluid at 4° C. The solution is warmed to 37° C. in a preheated water bath. The solution transforms in to viscous gel after 10 minutes of incubation. Upon cooling the gel to 4° C., it transforms into free flowing fluid again. The free flowing cold solution and the gel at 37° C. are visible when viewed using x-ray imaging equipment such as fluoroscope.

EXAMPLE 44

Preparation of Non-Crosslinked and Water Soluble Iodinated Albumin Derivative 1 g of albumin is dissolved in 10 ml 20 mM phosphate buffered saline pH 7.5. To this solution, 1 g 3,5-bis(acetylamino)-2,4,6-triiodobenzoic acid n-hydroxysuccimide ester, dissolved in 0.5 ml dimethyl sulfoxide is added (example 34). The reaction mixture is shaken for 10 minutes and the reaction is continued for 12 hours at room temperature. The reaction mixture is then poured in to 500 ml cold ethanol to precipitate iodinated albumin. The precipitated albumin is filtered and dried in vacuum at room temperature until constant weight. Alternatively, the reaction mixture may be lyophilized and then washed with 30 ml acetone 2 times to remove unreacted iodinated compound. Modified albumin shows at least 1% solubility in PBS solution.

EXAMPLE 45

Preparation of Radio-Opaque Polycarbonate Polyurethane
In a 250 ml conical flask containing Teflon™ coated magnetic stir bar, 10 g polycarbonate polyurethane, (Carbothane™ PC-3575A, Thermedics Corporation, MA, USA), 3 g iopamidol, and 90 g dimethyl acetamide (DMAC) are added. The mixture is stirred for 48 hours at room temperature until the polymer is completely dissolved in DMAC. The solution/suspension is used to coat medical devices to make them radio-opaque. Spry coating and dip coating methods may be used. Multiple coats may be applied to achieve a desired coating thickness. The coating thickness may range from few 2 microns to 2000 microns. Alternatively, the polymer solution is added to 2000 ml methanol with continuous stirring. The precipitated polymer is filtered and dried in vacuum oven at 60° C. until constant weight. The dried polymer is extruded into tubes using standard extrusion techniques. The extruded tube is clearly visible in medical x-ray imaging equipment. Such tubes could be used for making medical devices such as catheters and balloons used in MIS procedures.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims.

The invention claimed is:

1. A biodegradable radio-opaque composition for implantation in the animal body, the composition comprising:
    an aqueous solution comprising a thermoreversible polymer and a non-radioactive iodinated organic compound that is not covalently bonded to the polymer, with the solution being a liquid at a temperature below about 15° C. and forming a gel at physiological temperature, wherein the iodinated organic compound in the solution is 3 to 40 percent by weight.

2. The composition of claim 1 wherein the thermoreversible polymer comprises a copolymer of polyethylene oxide and polypropylene oxide.

3. The composition of claim 1 wherein the thermoreversible polymer comprises PLURONIC F127.

4. The composition of claim 1 wherein the thermoreversible polymer comprises polyethylene oxide and poly(lactic acid).

5. The composition of claim 1 wherein the iodinated organic compound is selected from the group consisting of iohexol, metrizamide, iopamidol, 3,5-bis(acetylamino)-2,4,6-triiodobenzoic acid, meglumine diatrizoate, iopentol, iopromide, triiodobenzoic acid, erythrosine, and ioversol.

6. The composition of claim 1, further comprising at least one bioactive compound.

7. The composition of claim 6, wherein the bioactive compound is selected from a group consisting of anti-viral agents, anti-infectives, anti-pruritics, anti-psychotics, cholesterol or lipid reducing agents, cell cycle inhibitors, anti-cancer agents, anti-parkinsonism drugs, HMG-CoA inhibitors, anti-restenosis agents, anti-inflammatory agents, anti-asthmatic agents, antihelmintics, immunosuppressives, muscle relaxants, anti-diuretic agents, vasodilators, beta- blockers, hormones, anti-depressants, decongestants, calcium channel blockers, growth factors, wound healing agents, analgesics and analgesic combinations, local anesthetics agents, antihistamines, sedatives, angiogenesis promoting agents, angiogenesis inhibiting agents, and tranquilizers.

8. A method of delivering a bioactive compound, the method comprising:
    providing the composition of claim 6 having the bioactive compound; and
    administering an injectable solution of the composition to a patient comprising a thermosensitive polymer, a non-radioactive iodinated organic compound that is not covalently bonded to the polymer, and the bioactive compound, with the solution being a liquid at a temperature below about 15° C.; and
    forming a gel at physiological temperature, wherein the iodinated organic compound in the solution is 3 to 40 percent by weight.

9. The method of claim 8 wherein the thermoreversible polymer comprises a copolymer of polyethylene oxide and polypropylene oxide.

10. The method of claim 8 wherein the iodinated organic compound is selected from the group consisting of iohexol, metrizamide, iopamidol, 3,5-bis(acetylamino)-2,4,6-triiodobenzoic acid, meglumine diatrizoate, iopentol, iopromide, triiodobenzoic acid, erythrosine, and ioversol.

11. A biodegradable radio-opaque composition for implantation in the animal body, the composition comprising:
    a solution comprising a thermoreversible polymer and a non-radioactive iodinated organic compound that is not covalently bonded to the polymer, with the solution being a liquid at a temperature between about 45 and about 55° C. and forming a gel at physiological temperature, wherein the iodinated organic compound in the solution is 3 to 40 percent by weight.

12. The composition of claim 11 wherein the thermoreversible polymer comprises a copolymer of polyethylene oxide and a polyhydroxyacid.

13. The composition of claim 11 wherein the copolymer comprises two blocks of polyethylene oxide and a block of polyhydroxyacid.

14. The composition of claim 11 wherein the thermoreversible polymer comprises gelatin.

15. The composition of claim 11 wherein the iodinated organic compound is selected from the group consisting of iohexol, metrizamide, iopamidol, 3,5-bis(acetylamino)-2,4, 6- triiodobenzoic acid, meglumine diatrizoate, iopentol, iopromide, triiodobenzoic acid, erythrosine, and ioversol.

16. The composition of claim 11, further comprising at least one bioactive compound.

17. A method of delivering a bioactive compound, the method comprising:
    providing the composition of claim 16 having the bioactive compound; and
    administering an injectable solution of the composition to a patient comprising a thermosensitive polymer, a non-radioactive iodinated organic compound that is not covalently bonded to the polymer, and the bioactive compound, with the solution being a liquid at a temperature between about 45° and about 55° C.; and
    forming a gel at physiological temperature, wherein the iodinated organic compound in the solution is 3 to 40 percent by weight.

18. The method of claim 17 wherein the thermoreversible polymer comprises a copolymer of polyethylene oxide and a polyhydroxyacid.

19. The method of claim 17 wherein the iodinated organic compound is selected from the group consisting of iohexol, metrizamide, iopamidol, 3,5-bis(acetylamino)-2,4,6-triiodobenzoic acid, meglumine diatrizoate, iopentol, iopromide, triiodobenzoic acid, erythrosine, and ioversol.

20. A biodegradable radio-opaque composition for injection implantation in the animal body, the composition comprising an injectable liquid stage and a biodegradable gel stage:
    the liquid stage being an aqueous solution at a temperature below about 15° C. or between about 45 and about 55° C. and comprising a thermoreversible polymer mixed with a water-soluble non-radioactive iodinated organic compound that is not covalently bonded to the polymer, wherein the iodinated organic compound in the solution is 3 to 40 percent by weight; and
    the biodegradable gel stage being a non-fluid hydrogel at physiological temperature and having the thermoreversible polymer mixed with the non-radioactive iodinated organic compound that is not covalently bonded to the polymer, wherein the iodinated organic compound in the biodegradable gel is 3 to 40 percent by weight.

21. The composition of claim 20 comprising one or more of the following:
    the thermoreversible polymer including a copolymer of polyethylene oxide and polypropylene oxide, PLURONIC F127, copolymer of polyethylene oxide and poly(lactic acid), copolymer of polyethylene oxide and a polyhydroxyacid;
    gelatin;
    the iodinated organic compound is selected from the group consisting of iohexol, metrizamide, iopamidol, 3,5-bis (acetylamino)-2,4,6-triiodobenzoic acid, meglumine diatrizoate, iopentol, iopromide, triiodobenzoic acid, erythrosine, and ioversol; or at least one bioactive compound selected from a group consisting of anti-viral agents, anti-infectives, anti-pruritics, anti-psychotics, cholesterol or lipid reducing agents, cell cycle inhibitors, anti-cancer agents, anti-parkinsonism drugs, HMG-CoA inhibitors, anti-restenosis agents, anti-inflammatory agents, anti-asthmatic agents, antihelmintics, immunosuppressives, muscle relaxants, anti-diuretic agents, vasodilators, beta-blockers, hormones, anti-depressants, decongestants, calcium channel blockers, growth factors, wound healing agents, analgesics and analgesic combinations, local anesthetics agents, antihistamines, sedatives, angiogenesis promoting agents, angiogenesis inhibiting agents, and tranquilizers.

* * * * *